United States Patent
Ross et al.

(10) Patent No.: US 12,264,198 B2
(45) Date of Patent: Apr. 1, 2025

(54) TANDEM DIABODY FOR CD16A-DIRECTED NK-CELL ENGAGEMENT

(71) Applicant: Affimed GmbH, Heidelberg (DE)

(72) Inventors: Thorsten Ross, Edingen-Neckarhausen (DE); Ivica Fucek, Hattersheim (DE); Kristina Ellwanger, Heidelberg (DE); Michael Weichel, Bischofsheim (DE); Uwe Reusch, Maikammer (DE); Stefan Knackmuss, Planckstadt (DE); Erich Rajkovic, Schriessheim (DE); Martin Treder, Heidelberg (DE)

(73) Assignee: AFFIMED GMBH, Mannheim (DE)

( * ) Notice: Subject to any disclaimer, the term of this patent is extended or adjusted under 35 U.S.C. 154(b) by 641 days.

(21) Appl. No.: 17/510,738

(22) Filed: Oct. 26, 2021

(65) Prior Publication Data

US 2022/0041717 A1  Feb. 10, 2022

Related U.S. Application Data

(63) Continuation of application No. 16/520,218, filed on Jul. 23, 2019, now Pat. No. 11,180,558, which is a continuation of application No. PCT/EP2018/054989, filed on Feb. 28, 2018.

(30) Foreign Application Priority Data

Feb. 28, 2017  (EP) ..................... 17158566
Jun. 2, 2017   (EP) ..................... 17174407

(51) Int. Cl.
  *C07K 16/28*   (2006.01)
  *A61P 35/00*   (2006.01)

(52) U.S. Cl.
  CPC .......... *C07K 16/283* (2013.01); *A61P 35/00* (2018.01); *C07K 2317/31* (2013.01); *C07K 2317/565* (2013.01); *C07K 2317/622* (2013.01); *C07K 2317/626* (2013.01); *C07K 2317/732* (2013.01); *C07K 2317/92* (2013.01)

(58) Field of Classification Search
  CPC .............. C07K 16/283; C07K 2317/31; C07K 2317/565; C07K 2317/622; C07K 2317/626; C07K 2317/732; C07K 2317/92; C07K 2317/62; C07K 16/2878; A61P 35/00; A61K 2039/505
  See application file for complete search history.

(56) References Cited

U.S. PATENT DOCUMENTS

| 7,129,330 B1 | 10/2006 | Little et al. |
| 2005/0089519 A1 | 4/2005 | Kipriyanov et al. |
| 2009/0214574 A1* | 8/2009 | Hoffmann .......... A61K 47/6879 435/69.6 |

FOREIGN PATENT DOCUMENTS

| EP | 2361936 A1 | 8/2011 | |
| WO | 2013013700 A1 | 1/2013 | |
| WO | WO 2013/013700 * | 1/2013 | ............. C07K 16/16 |
| WO | 2016177846 A1 | 11/2016 | |

OTHER PUBLICATIONS

Evaluate, "Affimed Provides Update on NK-Cell Immuno-Oncology Platform", Jan. 11, 2017.
Thorsten Gantke, et al., "AFM26—Targeting BCMA for NK cell-mediated immunotherapy of multiple myeloma", 59th meeting of the American Society of Hematology, Dec. 12, 2017.
Uwe Reusch et al., "A novel tetravalent bispecific TandAb {CD30/CD16A) efficiently recruits NK cells for the lysis of CD30+ tumor cells", MABS, vol. 6, No. 3, Mar. 26, 2014, pp. 727-738.
Achim Rothe, et al., "A phase 1 study of the bispecific anti-CD30/CD16A antibody construct AFM13 in patients with relapsed or refractory Hodgkin lymphoma", Blood, vol. 125, No. 26, Jun. 25, 2015, pp. 4024-4031.
International Search Report dated Apr. 3, 2018 issued in PCT/EP2018/054989.

\* cited by examiner

*Primary Examiner* — Nelson B Moseley, II
(74) *Attorney, Agent, or Firm* — Perkins Coie LLP; Viola Kung

(57) ABSTRACT

The invention relates to a multispecific antigen-binding molecule specifically binding to CD16A and consisting of two polypeptide chains, wherein each polypeptide chain comprises at least four variable domains from the N-terminus to the C-terminus in the order: VH_BCMA-VL_CD16A-VH_CD16A-VL_BCM.

11 Claims, 10 Drawing Sheets

Specification includes a Sequence Listing.

SEQUENCE LISTING

<160> NUMBER OF SEQ ID NOS: 21

<210> SEQ ID NO 1
<211> LENGTH: 8
<212> TYPE: PRT
<213> ORGANISM: artificial sequence
<220> FEATURE:
<223> OTHER INFORMATION: CDR

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: artificial sequence
<220> FEATURE:
<223> OTHER INFORMATION: CDR

<400> SEQUENCE: 2

Ile Glu Pro Met Tyr Gly Ser Thr
1               5

<210> SEQ ID NO 3
<211> LENGTH: 13
<212> TYPE: PRT
<213> ORGANISM: artificial sequence
<220> FEATURE:
<223> OTHER INFORMATION: CDR

<400> SEQUENCE: 3

Ala Arg Gly Ser Ala Tyr Tyr Tyr Asp Phe Ala Asp Tyr
1               5                   10

<210> SEQ ID NO 4
<211> LENGTH: 6
<212> TYPE: PRT
<213> ORGANISM: artificial sequence
<220> FEATURE:
<223> OTHER INFORMATION: CDR

<400> SEQUENCE: 4

```
Asn Ile Gly Ser Lys Asn
1               5

<210> SEQ ID NO 5
<211> LENGTH: 4
<212> TYPE: PRT
<213> ORGANISM: artificial sequence
<220> FEATURE:
<223> OTHER INFORMATION: cdr

<400> SEQUENCE: 5

Gln Asp Asn Lys
1

<210> SEQ ID NO 6
<211> LENGTH: 9
<212> TYPE: PRT
<213> ORGANISM: artificial sequence
<220> FEATURE:
<223> OTHER INFORMATION: CDR

<400> SEQUENCE: 6

Gln Val Trp Asp Asn Tyr Ser Val Leu
1               5

<210> SEQ ID NO 7
<211> LENGTH: 8
<212> TYPE: PRT
<213> ORGANISM: artificial sequence
<220> FEATURE:
<223> OTHER INFORMATION: CDR

<400> SEQUENCE: 7

Ile Asn Pro Ser Gly Gly Ser Thr
1               5

<210> SEQ ID NO 8
<211> LENGTH: 120
<212> TYPE: PRT
<213> ORGANISM: artificial sequence
<220> FEATURE:
<223> OTHER INFORMATION: vh

<400> SEQUENCE: 8

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ala Ile Glu Pro Met Tyr Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
        115                 120

<210> SEQ ID NO 9
```

```
<211> LENGTH: 106
<212> TYPE: PRT
<213> ORGANISM: artificial sequence
<220> FEATURE:
<223> OTHER INFORMATION: vl

<400> SEQUENCE: 9

Ser Tyr Val Leu Thr Gln Pro Ser Ser Val Ser Ala Pro Gly Gln
1               5                   10                  15

Thr Ala Thr Ile Ser Cys Gly Gly His Asn Ile Gly Ser Lys Asn Val
            20                  25                  30

His Trp Tyr Gln Gln Arg Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
            100                 105

<210> SEQ ID NO 10
<211> LENGTH: 120
<212> TYPE: PRT
<213> ORGANISM: artificial sequence
<220> FEATURE:
<223> OTHER INFORMATION: vh

<400> SEQUENCE: 10

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Asp Phe Ala Asp Tyr Trp Gly Gln
            100                 105                 110

Gly Thr Leu Val Thr Val Ser Ser
        115                 120

<210> SEQ ID NO 11
<211> LENGTH: 8
<212> TYPE: PRT
<213> ORGANISM: homo sapiens

<400> SEQUENCE: 11

Ser Phe Phe Pro Pro Gly Tyr Gln
1               5

<210> SEQ ID NO 12
<211> LENGTH: 11
<212> TYPE: PRT
<213> ORGANISM: artificial sequence
```

-continued

```
<220> FEATURE:
<223> OTHER INFORMATION: affinity tag

<400> SEQUENCE: 12

Ala Ala Ala Gly Ser His His His His His
1               5                   10

<210> SEQ ID NO 13
<211> LENGTH: 4
<212> TYPE: PRT
<213> ORGANISM: artificial sequence
<220> FEATURE:
<223> OTHER INFORMATION: linker

<400> SEQUENCE: 13

Gly Gly Ser Gly
1

<210> SEQ ID NO 14
<211> LENGTH: 5
<212> TYPE: PRT
<213> ORGANISM: artificial sequence
<220> FEATURE:
<223> OTHER INFORMATION: linker

<400> SEQUENCE: 14

Gly Gly Ser Gly Gly
1               5

<210> SEQ ID NO 15
<211> LENGTH: 6
<212> TYPE: PRT
<213> ORGANISM: artificial sequence
<220> FEATURE:
<223> OTHER INFORMATION: linker

<400> SEQUENCE: 15

Gly Gly Ser Gly Gly Ser
1               5

<210> SEQ ID NO 16
<211> LENGTH: 9
<212> TYPE: PRT
<213> ORGANISM: artificial sequence
<220> FEATURE:
<223> OTHER INFORMATION: linker

<400> SEQUENCE: 16

Gly Gly Ser Gly Gly Ser Gly Gly Ser
1               5

<210> SEQ ID NO 17
<211> LENGTH: 114
<212> TYPE: PRT
<213> ORGANISM: artificial sequence
<220> FEATURE:
<223> OTHER INFORMATION: vh

<400> SEQUENCE: 17

Gln Val Gln Leu Val Gln Ser Gly Ala Glu Val Lys Thr Pro Gly Glu
1               5                   10                  15

Pro Leu Lys Ile Ser Cys Lys Gly Ser Gly Tyr Ser Phe Thr Asp Ser
                20                  25                  30

Trp Ile Gly Trp Val Arg Gln Met Pro Gly Lys Gly Leu Glu Trp Met
            35                  40                  45
```

```
Gly Ile Ile Tyr Ala Gly Asp Ser Asp Ala Arg Tyr Ser Pro Ser Phe
        50                  55                  60

Gln Gly Gln Val Thr Ile Ser Ala Asp Thr Ser Thr Ser Thr Val Tyr
65                      70                  75                  80

Leu Gln Trp Ser Ser Leu Lys Ala Ser Asp Thr Ala Met Tyr Tyr Cys
                    85                  90                  95

Ala Arg Asn Phe Gly Asp His Trp Gly Gln Gly Thr Leu Val Thr Val
                100                 105                 110

Ser Ser

<210> SEQ ID NO 18
<211> LENGTH: 106
<212> TYPE: PRT
<213> ORGANISM: artificial sequence
<220> FEATURE:
<223> OTHER INFORMATION: vl

<400> SEQUENCE: 18

Ser Tyr Glu Leu Thr Gln Ser Pro Ser Val Ser Val Ala Pro Gly Gln
1               5                   10                  15

Thr Ala Arg Ile Phe Cys Gly Gly Asp Asn Ile Gly Ser Lys Asn Val
                20                  25                  30

His Trp Tyr Gln Gln Lys Pro Gly Gln Ala Pro Val Leu Val Ile Tyr
            35                  40                  45

Arg Asp Ser Asn Arg Pro Ser Gly Ile Pro Glu Arg Phe Ser Gly Ala
        50                  55                  60

Asn Ser Glu Asn Thr Ala Thr Leu Thr Ile Ser Arg Ala Gln Ala Gly
65                  70                  75                  80

Asp Glu Ala Asp Tyr Tyr Cys Gln Val Trp Asp Ser Arg Thr Tyr Val
                85                  90                  95

Phe Gly Thr Gly Thr Lys Leu Thr Val Leu
                100                 105

<210> SEQ ID NO 19
<211> LENGTH: 249
<212> TYPE: PRT
<213> ORGANISM: artificial sequence
<220> FEATURE:
<223> OTHER INFORMATION: scFv

<400> SEQUENCE: 19

Gln Val Gln Leu Val Gln Ser Gly Ala Glu Val Lys Thr Pro Gly Glu
1               5                   10                  15

Pro Leu Lys Ile Ser Cys Lys Gly Ser Gly Tyr Ser Phe Thr Asp Ser
                20                  25                  30

Trp Ile Gly Trp Val Arg Gln Met Pro Gly Lys Gly Leu Glu Trp Met
            35                  40                  45

Gly Ile Ile Tyr Ala Gly Asp Ser Asp Ala Arg Tyr Ser Pro Ser Phe
        50                  55                  60

Gln Gly Gln Val Thr Ile Ser Ala Asp Thr Ser Thr Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Asn Phe Gly Asp His Trp Gly Gln Gly Thr Leu Val Thr Val
                100                 105                 110

Ser Ser Gly Gly Ser Gly Gly Ser Gly Gly Ser Gly Gly
            115                 120                 125
```

```
Ser Gly Gly Ser Ser Tyr Glu Leu Thr Gln Ser Pro Ser Val Ser Val
        130                 135                 140

Ala Pro Gly Gln Thr Ala Arg Ile Phe Cys Gly Gly Asp Asn Ile Gly
145                 150                 155                 160

Ser Lys Asn Val His Trp Tyr Gln Gln Lys Pro Gly Gln Ala Pro Val
                165                 170                 175

Leu Val Ile Tyr Arg Asp Ser Asn Arg Pro Ser Gly Ile Pro Glu Arg
            180                 185                 190

Phe Ser Gly Ala Asn Ser Glu Asn Thr Ala Thr Leu Thr Ile Ser Arg
        195                 200                 205

Ala Gln Ala Gly Asp Glu Ala Asp Tyr Tyr Cys Gln Val Trp Asp Ser
    210                 215                 220

Arg Thr Tyr Val Phe Gly Thr Gly Thr Lys Leu Thr Val Leu Ala Ala
225                 230                 235                 240

Ala Gly Ser His His His His His His
                245
```

<210> SEQ ID NO 20
<211> LENGTH: 192
<212> TYPE: PRT
<213> ORGANISM: homo sapiens

<400> SEQUENCE: 20

```
Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
                20                  25                  30

Gly Ala Tyr Ser Pro Glu Asp Asn Ser Thr Gln Trp Phe His Asn Glu
            35                  40                  45

Ser Leu Ile Ser Ser Gln Ala Ser Ser Tyr Phe Ile Asp Ala Ala Thr
        50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Phe
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190
```

<210> SEQ ID NO 21
<211> LENGTH: 12

```
<212> TYPE: PRT
<213> ORGANISM: artificial sequence
<220> FEATURE:
<223> OTHER INFORMATION: linker

<400> SEQUENCE: 21

Gly Gly Ser Gly Gly Ser Gly Gly Ser Gly Gly Ser
1               5                   10
```

TANDEM DIABODY FOR CD16A-DIRECTED NK-CELL ENGAGEMENT

This application is a continuation of U.S. application Ser. No. 16/520,218, filed Jul. 23, 2019, which is a continuation of PCT/EP2018/054989, filed Feb. 28, 2018; which claims the priority of EP 17158566.4, filed Feb. 28, 2017, and EP 17174407.1, filed Jun. 2, 2017. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Jul. 24, 2019, and a size of 4.5 kilobytes. The Sequence Listing filed via EFS-Web is part of the specification and is hereby incorporated in its entirety by reference herein.

FIELD OF THE INVENTION

The invention relates to multispecific antigen-binding molecules for engaging natural killer (NK) cells for triggering NK-cell cytotoxicity via the CD16A (FcγRIIIA) antigen expressed on NK-cells. The invention describes a novel Fv-domain protein conformation for inducing a potent antibody-dependent cell-mediated cytotoxicity (ADCC). In an embodiment, the invention further relates to a tandem diabody comprising two anti-CD16A in the novel Fv-domain protein conformation. An embodiment of the invention is an anti-BCMA/CD16A multispecific antigen molecule and its use for the treatment of BCMA$^+$ diseases, such as, for example, multiple myeloma.

BACKGROUND OF THE INVENTION

NK-cells are potent cytotoxic immune effector cells of the innate immune system. The cytotoxic potential of NK-cells can be utilized in cancer immunotherapy by redirecting NK-cell lysis to tumor cells and stimulating the activating receptor CD16A, also known as FcγRIIIA, expressed on the cell surface of NK-cells. A bispecific anti-CD30/CD16A tandem diabody in phase 2 clinical development has been constructed for the treatment of certain CD30-positive B- and T-cell malignancies, including Hodgkin Lymphoma (Rothe et al.; Blood 2015, 125(26):4024-4031; Reusch et al.; MABS 2014, 6(3):727-738). The molecule comprises two binding sites for CD30, an epitope found on the tumor cells of various lymphomas, and two binding sites for CD16A. The NK-cell expresses various stimulatory and inhibitory receptors that regulate its activity, that allow it to distinguish between healthy cells and infected or transformed cells.

When the NK-cell via its CD16A receptor is engaged by the tandem diabody with a CD30-positive tumor cell (via its CD30 antigen) it forms an immunological synapse, which generates a strong activating signal. Simultaneous engagement of the tandem diabody with the NK-cell via its CD16A receptor and a tumor cell via CD30 induces CD16A-mediated NK-cell activation and the formation of an immunological synapse resulting in polarized exocytosis of lytic granules containing perforin and granzymes, and surface expression of FasL, TRAIL, and TNF-α, which induces tumor cell death by initiating a succession of further enzyme activities (the caspase cascade.) resulting in tumor cell apoptosis (programmed cell death).

Thus, such bispecific tandem diabody is able to selectively redirect NK-cell lysis to launch an attack and eliminate cancer cells. In contrast, full-length antibodies of the IgG isotype bind through their Fc region activating and inhibitory Fcγ receptors, including CD16A, CD16B (FcγRIIIB), CD32A (FcγRIIA), CD32B (FcγRIIB) and CD64 (FcγRI). However, the tandem diabody having specificity for CD16A selectively targets the activating subtype CD16A, which is found on NK-cells and macrophages, but not on neutrophils. Furthermore, the NK-cell engaging tandem diabody interacts bivalently with CD16A resulting in approximately 1,000-fold higher affinity compared with regular antibodies.

For the binding of NK-cells, an antibody that selectively interacts with CD16A with high affinity has been constructed and described in WO 2006/125668. The NK-cell engaging tandem diabody incorporating said anti-CD16A antibody and a target antigen-specific antibody, e.g. CD30, binds to a target cell antigen molecule with two of its binding sites and simultaneously interacts with the CD16A receptor with the other two binding sites. This cell-cell cross-linking event stimulates CD16A signaling and initiates the cytotoxic activity of the respective NK-cell.

Hence, directing NK-cells for tumor cell lysis using multispecific antibodies is considered a potent immunotherapeutic approach with reduced toxicity and manageable safety profile (Rothe et al., 2015).

CD16A is an activating receptor triggering the cytotoxic activity of NK cells. The affinity of antibodies for CD16A directly correlates with their ability to trigger NK cell activation, thus reducing the antibody dose required for activation.

Therefore, it exists a need for increasing affinity for CD16A engaging antibodies for triggering an increased NK cell cytotoxicity.

The cytotoxic activity of NK cells can be increased by increasing the avidity through multivalent binding to CD16A, e.g. bivalent binding to CD16A.

However, bivalent and multivalent binding to CD16A may result in cross linking of a NK cell to another NK cell via the two CD16A binding arms of the antibody. This causes NK cell activation and induction of fratricide (NK-NK cell lysis) ultimately resulting in efficient NK cell depletion in vivo, as previously described using a CD16-directed murine IgG antibody (3G8) that is bivalent for CD16A in rhesus macaques and tamarins (Choi et al., Immunology, 2008, 124:215-222; Yoshida et al., Frontier in Microbiology, 2010, 1:128). Hence, cross-linking of NK cells and induction of NK-NK lysis reduces the number of effector cells available to mediate ADCC and impairs therapeutic antibody efficacy.

Thus, it is an object of the invention to provide a CD16A-engaging antibody capable of bivalent interaction with CD16A on NK cells and hence with increased binding affinity and cytotoxic potency but incapable of inducing NK-NK-cell lysis.

SUMMARY OF THE INVENTION

It has now been found that the cytotoxic activity of NK-cells can be increased by a tetravalent tandem diabody, when in the tandem diabody a pair of two juxtaposed anti-CD16A antigen-binding sites is positioned inside in the center and two anti-tumor antigen-binding sites are positioned outside, peripheral to the CD16A antigen-binding sites and the variable domains are positioned within each polypeptide chain from the N-terminus to the C-terminus of the polypeptide in the order: VH_TA-VL_CD16A-VH_CD16A-VL_TA (VH=variable heavy chain, VL=variable light chain; TA=tumor antigen; FIG. 1).

Such arrangement of antigen-binding sites prevents cross-linking of NK-cells via CD16A and, thereby, does not induce NK-cell lysis. On the other hand, the antigen-binding molecule bivalently binds to the NK-cell with two anti-CD16A antigen-binding sites, thereby increasing the cytotoxic potency through the higher avidity.

Structural analyses of bivalent diabodies have suggested that antigen-binding sites in such molecules are positioned at opposite sides and face away from each other in a conformation that allows efficient cell-cell cross-linking following specific binding of two surface antigens (Perisic et al., Structure, 1994, 2(12):1217-26). In agreement with this, a comparable bivalent anti-CD16A diabody consisting of the same anti-CD16A domains in the same domain orientation as employed in the center of the tetravalent antigen-binding molecule according to the invention induces NK-NK cell cross-linking and NK-NK cell depletion in vitro (Example 4, Table 6). The inability of the tetravalent tandem diabody according to the invention to induce NK-cell depletion in vitro suggests that the particular protein configuration, i.e. two juxtaposed anti-CD16A antigen-binding sites positioned in the center and two anti-tumor antigen-binding sites positioned outside, peripherally to the CD16A antigen-binding sites in the order: VH_TA-VL_CD16A-VH_CD16A-VL_TA (FIG. 1), according to the invention surprisingly results in a conformation distinct from diabodies that prevents NK-NK cell lysis but increases avidity through bivalent CD16A binding.

Hence, such particular tetravalent tandem diabody with a pair of CD16A antigen-binding sites in the center of the polypeptide, provides a protein conformation in which both CD16A-directed Fv domains are positioned such that bivalent binding is optimal but NK-cell-NK-cell cross-linking is prevented. Consequently, such antigen-binding molecule exhibits increased avidity and cytotoxic potency but does not induce NK-cell depletion.

Furthermore, the failure to induce NK-cell-NK-cell lysis may allow such antigen-binding molecule to be used in combination with cellular NK-cell therapies, e.g. by mixing allogeneic or autologous NK-cells and antibody ex vivo before infusion into patients (adoptive transfer).

Further, due to high plasma levels of IgG (physiological levels are typically about 10 mg/ml) CD16A-engaging antibodies face competition for CD16A binding with the Fc-domains of IgGs, thereby increasing the required dose of therapeutic antibody. Competition with plasma IgGs is even more pronounced in diseases which are characterized by high levels of plasma IgGs such as multiple myeloma (MM). Hence, CD16A-mediated stimulation of cytotoxic activity of NK-cells using bispecific antigen-binding molecules or classical antibody formats that incorporate an Fc region of IgG is reduced in presence of serum IgG which competes through its Fc region for CD16A binding on NK-cells.

The invention further provides a CD16A Fv-domain recognizing an epitope on CD16A distinct from the binding site for Fc thereby reducing competition by polyclonal IgG for CD16A.

Notably, positioning of a pair of juxtaposed CD16A-directed Fv domains in central position of the antigen-binding molecule impacts NK-cell binding and results in reduced competition by polyclonal IgG for CD16A. Example 2 shows that presence of IgG reduces the affinity of the CD16A engaging tandem diabody independent of the domain orientation within the molecule. However, the tandem diabodies are differently affected and the tandem diabody with the orientation positioning the CD16A domains in the center of the tandem diabody (variant 4) exhibits higher NK-cell binding affinity in presence of polyclonal IgG due to reduced competition for CD16A binding. Similarly, cytotoxic activity in vitro of tandem diabodies is differently affected by presence of physiological IgG levels depending on the positioning of the CD16A domains within the molecule with the tandem diabody variant 4 exhibiting the higher potency and reduced loss off potency in presence of polyclonal IgG.

In addition, it has been found for tandem diabodies that retention on the NK-cell surface was not affected by addition of polyclonal IgG, as the rate of dissociation was similar in presence and absence of IgG (Example 2). This suggests that polyclonal IgG cannot displace tandem diabody from NK-cells once bound, because the tandem diabody binds to an epitope distinct from the binding site of IgG on CD16A. Consequently, the protein conformation resulting from the domain orientation within the tandem diabody in variant 4 (FIG. 2) may be uniquely suited to target and bivalently bind NK-cells in presence of serum IgG, e.g. at physiological IgG concentrations and in particular in plasma cell disorders characterized by high level production of monoclonal immunoglobulin. In particular, the observed retention of tandem diabody on NK-cells and the lack of IgG interference with its dissociation suggest tandem diabody in variant 4 (FIG. 2) may be used in combination with cellular NK-cell products, e.g. by mixing NK-cells and antibody ex vivo before infusion into patients (adoptive NK-cell transfer). Because classical IgG-based therapeutic antibody formats interact only weakly with CD16A and directly compete with serum IgG for CD16A binding, it is expected that such antibodies would rapidly dissociate from NK-cells when mixed with NK-cells before infusion into patients. In contrast, because of its prolonged NK-cell surface retention CD16A-directed tandem diabody in variant 4 (FIG. 2) is expected to enable novel combination approaches with cellular NK-cell products that have, so far, been impossible to realize.

In summary, the present invention provides a particular protein conformation in the format of a tetravalent tandem diabody for a CD16A Fv-domain binding to an epitope distinct from that of IgG Fc-domains for increasing NK cell cytotoxicity by bivalent binding to an NK cell while NK cell depletion due to NK-to-NK-cell cross-linking is prevented and competition for CD16A by polyclonal IgG is reduced.

Therefore, a first embodiment of the invention refers to a dimeric multispecific antigen-binding molecule, preferably a tandem diabody, specifically binding to CD16A and a target cell antigen different from CD16A consisting of two polypeptide chains, wherein each polypeptide chain comprises at least four variable domains from the group consisting of (i) a heavy chain variable domain specific for CD16A (VH_CD16A) comprising a heavy chain CDR1 having the amino acid sequence set forth in SEQ ID NO:1; a heavy chain CDR2 having the amino acid sequence set forth in SEQ ID NO:2; a heavy chain CDR3 having the amino acid sequence set forth in SEQ ID NO:3, (ii) a light chain variable domain specific for CD16A (VL_CD16A) comprising a light chain CDR1 having an amino acid sequence set forth in SEQ ID NO:4; a light chain CDR2 having an amino acid sequence set forth in SEQ ID NO:5; and a light chain CDR3 having an amino acid sequence set forth in SEQ ID NO:6, (iii) a heavy chain variable domain specific for the target cell antigen (VH_TA), and (iv) a light chain variable domain specific for the target cell antigen (VL_TA), wherein these variable domains are linked one after another by peptide linkers L1, L2 and L3 and positioned within each of the two polypeptide chains from the N-terminus to the C-terminus in the order: VH_TA-L1-VL_CD16A-L2-VH_CD16A-L3-VL_TA. Preferably, the peptide linkers L1, L2 and L3 consist of 12 or less amino acid residues.

Furthermore, novel therapies are needed to achieve long-lasting remissions in a greater number of patients, despite recent advances in the treatment of multiple myeloma (MM). NK-cells play a key role in the immune response to MM and have been implicated in the clinical efficacy of current standard of care interventions, including IMiDs, proteasome inhibitors, recently approved immunotherapies and autologous stem cell transplantation (ASCT). Numerous strategies are being developed to enhance the natural NK-cell cytotoxicity against myeloma cells, which is frequently dysregulated in MM. Approaches include modulation of activity, through cytokine stimulation or immune checkpoint targeting, and adoptive transfer of culture expanded NK-cells in ASCT-eligible MM. While highly attractive, these approaches are non-targeted, as they rely on the natural cytotoxicity of NK-cells, and may benefit from antigen-specific retargeting and effector activation.

MM is a plasma cell malignancy, characterized by high level production of monoclonal immunoglobulin (M-protein): Serum levels of M-protein in IgG-type myeloma can be as high as 100 mg/mL or higher, wherein a serum level of about 10 mg/mL is typical for a healthy individual. Approximately 50% of tumors produce IgG M-protein, wherein approximately 50% are IgG1 or IgG3.

Due to the competition by serum IgG for CD16A at physiological concentrations (i) the potency of antibodies to induce NK-cell-mediated antibody-dependent cell-mediated cytotoxicity (ADCC) can be reduced which results in increased therapeutic doses needed and (ii) the threshold of target antigen levels needed to elicit NK-cell activation upon encounter of target antigen-positive cells is increased, as IgG competition effectively reduces the number of CD16A receptors available for cell-cell cross-linking. As a consequence, IgG competition reduces antibody-induced NK-cell activity towards target cells that express low levels of target antigen. This can be inferred from studies reporting increased ADCC activity towards low antigen-expressing cells of NK-cells stimulated with antibodies bearing Fc mutations that increase affinity of CD16A binding.

BCMA (B-cell maturation antigen, CD269) is considered a highly attractive target antigen for immunotherapy of MM. BCMA is described as universally expressed on myeloma cells.

Therefore, a further object of the invention is to provide an antibody that induces a potent and efficacious ADCC in myeloma, in particular in the presence of IgG M-protein.

In a further aspect the present invention provides a novel tetravalent bispecific tandem diabody (TandAb) that binds to BCMA and CD16A. This tandem diabody incorporates the affinity-improved anti-CD16A Fv-domain and interacts bivalently with NK-cells resulting in high avidity and prolonged cell surface retention that is unaffected by the presence of polyclonal IgG. Due to the novel Fv-domain protein conformation of the particular CD16A engaging domains the tandem diabody potently induces NK-cell mediated in vitro lysis even in presence of polyclonal IgG. This suggests that the tandem diabody, in contrast to classical mAbs, retains ADCC activity at low antibody concentrations in presence of serum IgG and despite high levels of IgG M-protein occurring in about half of MM patients.

This has been achieved according to the invention by positioning a pair of juxtaposed anti-CD16A antigen-binding sites inside into the center of the tandem diabody and the BCMA antigen-binding sites N-terminally and C-terminally peripheral thereto such that the variable domains are arranged within the polypeptide chain of the tandem diabody in the order VH_(BCMA)-VL_(CD16A)-VH_(CD16A)-VL_(BCMA).

Therefore, such BCMA/CD16A tandem diabody disclosed by the present invention is a highly potent drug candidate for MM treatment.

INCORPORATION BY REFERENCE

All publications, patents, and patent applications mentioned in this specification are herein incorporated by reference to the same extent as if each individual publication, patent, or patent application is specifically and individually indicated to be incorporated by reference.

L1, L2, L3: Linker; VH CD16A: heavy chain variable domain binding to CD16A; VL CD16A: light chain variable domain binding to CD16A; VH BCMA: heavy chain variable domain binding to BCMA; and VL BCMA: light chain variable domain binding to BCMA; sp: signal peptide; Ta: affinity tag.

Figure 3:
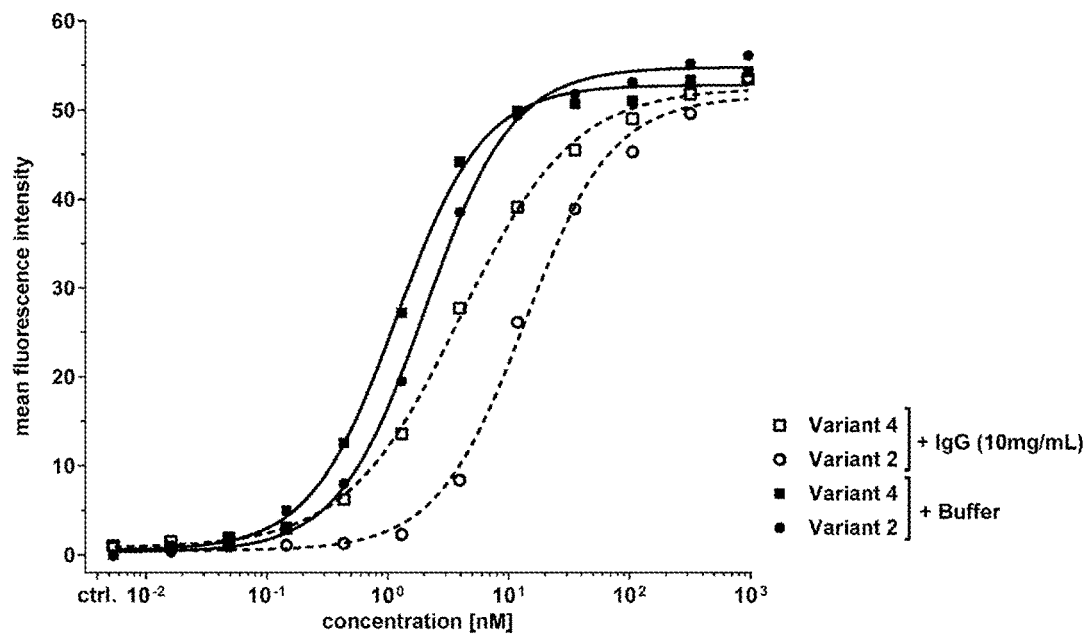
Figure 4:
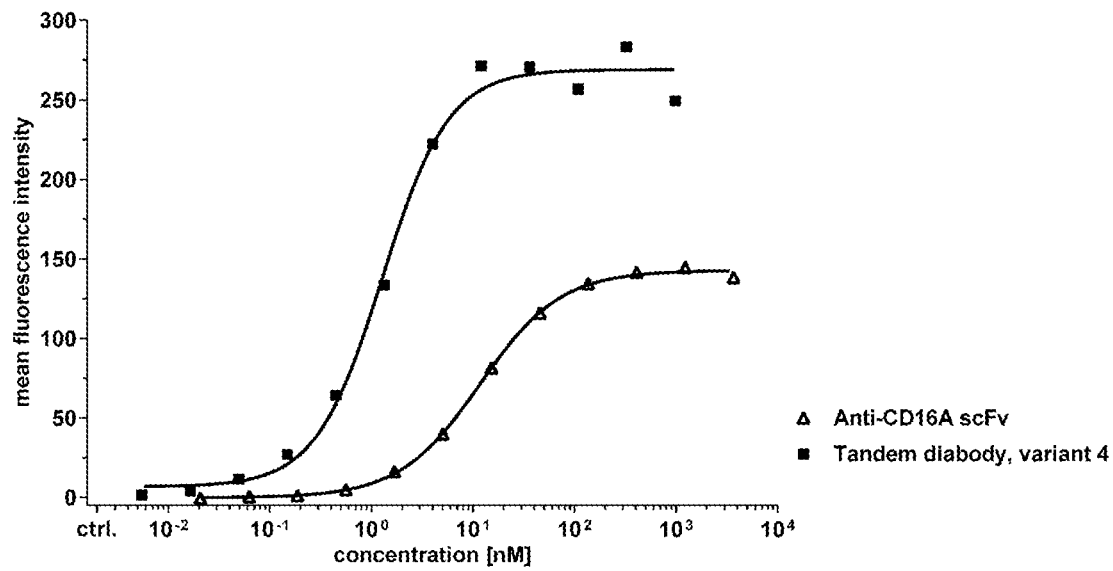
Figure 5:
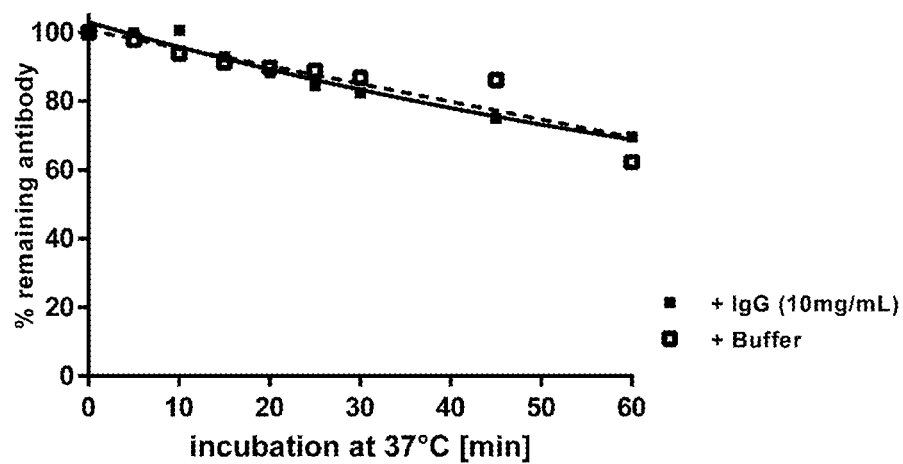
Figure 6:
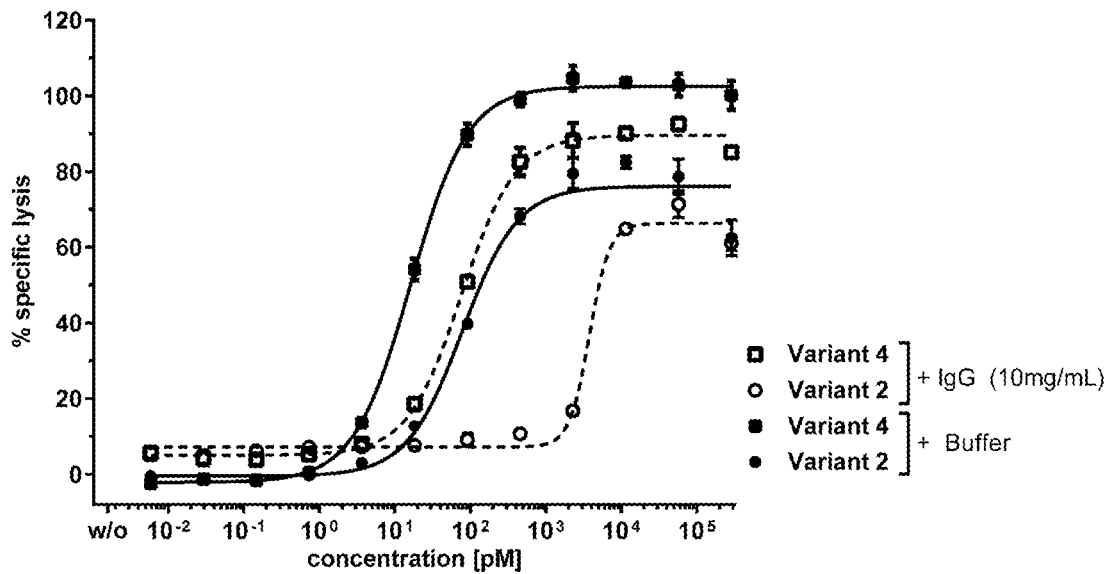
Figure 7:
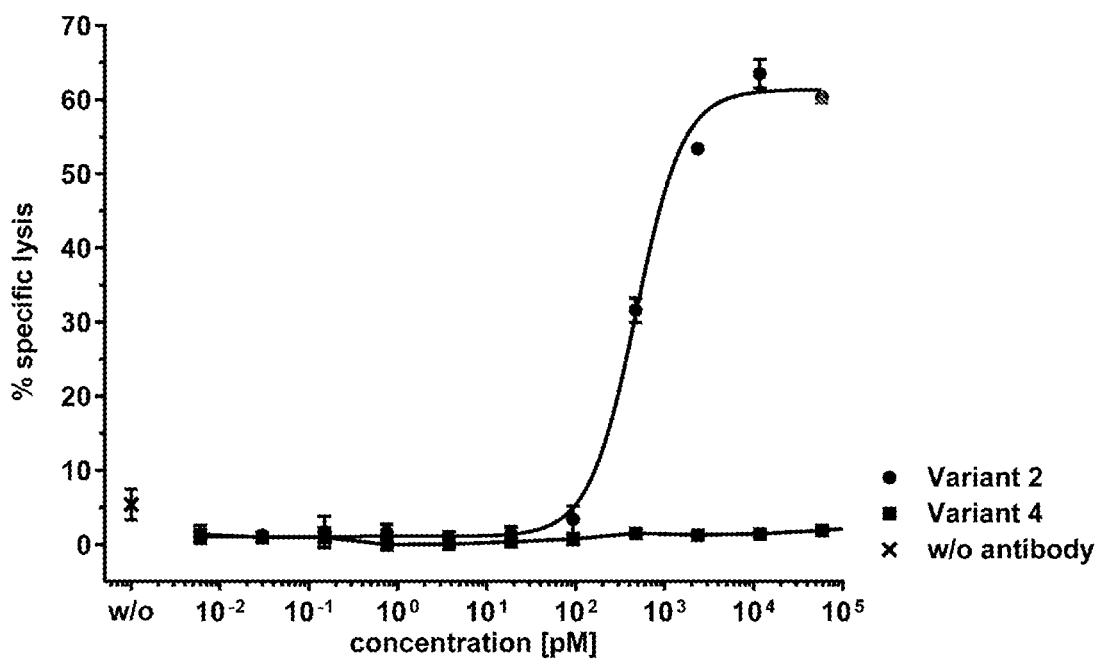
Figure 8:
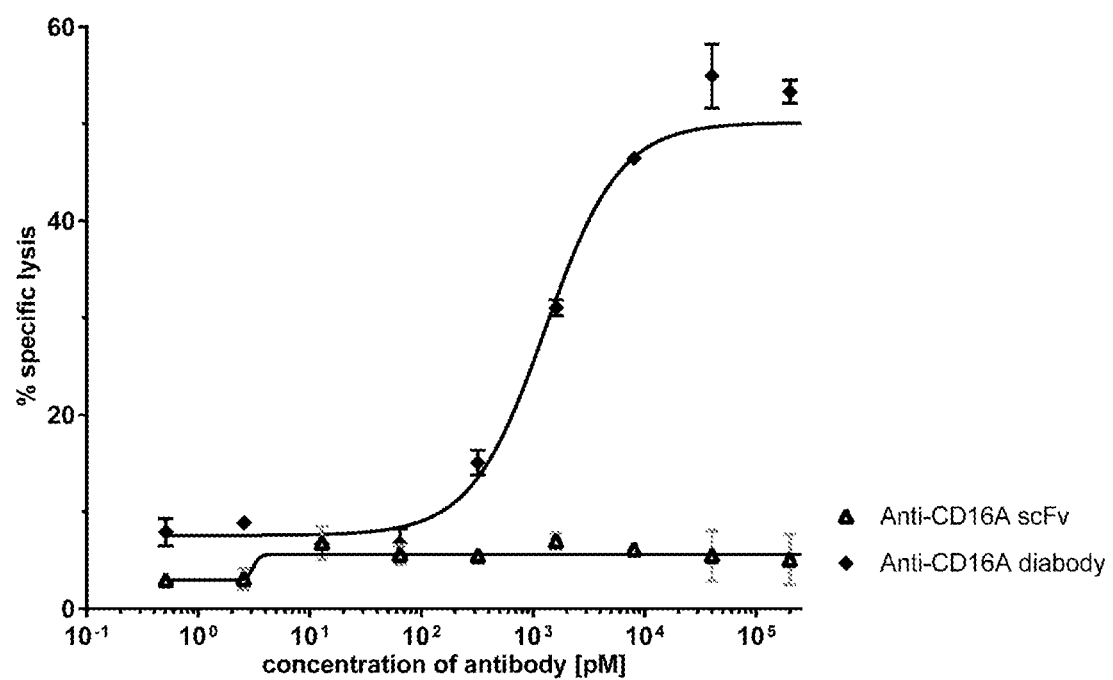
Figure 9:
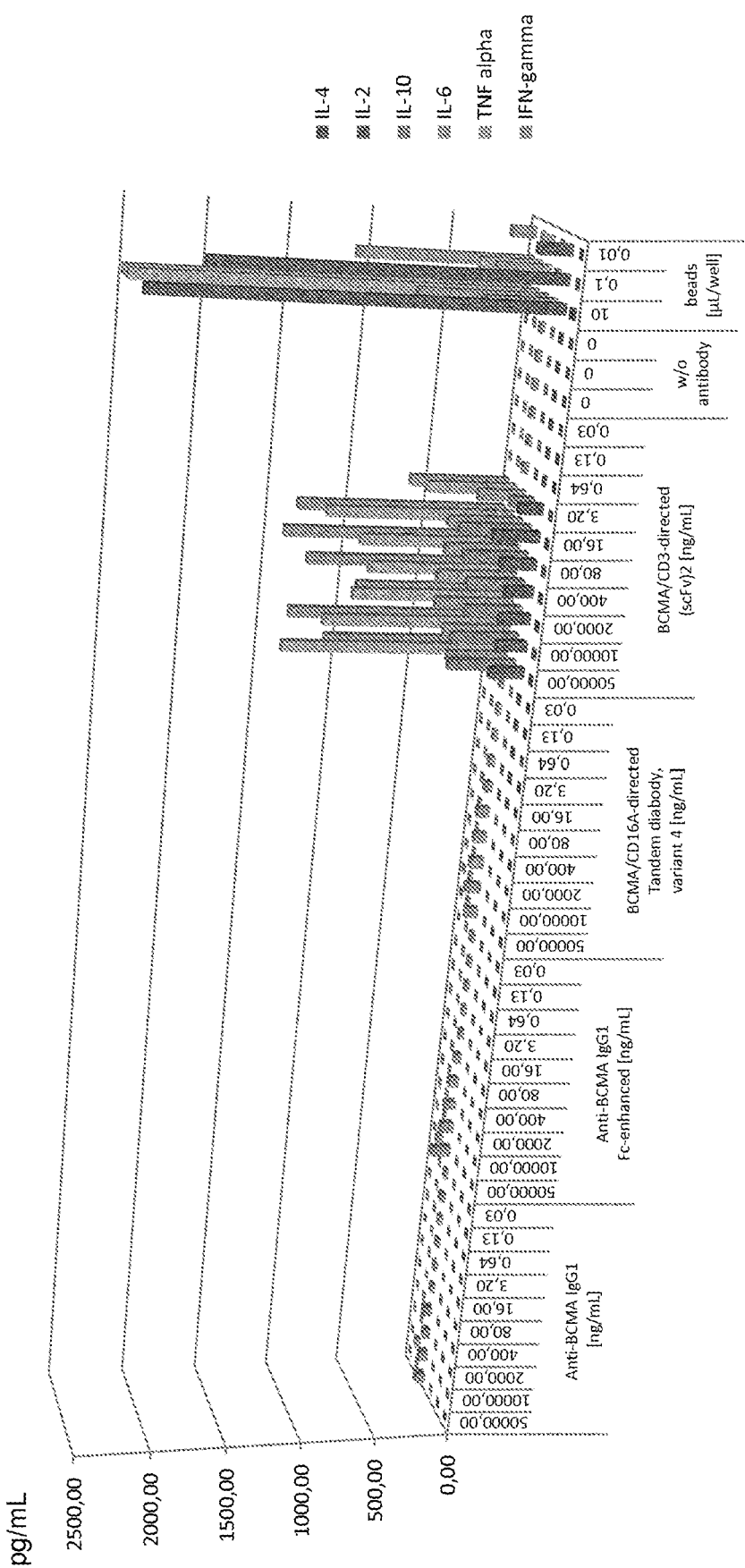
Figure 10:
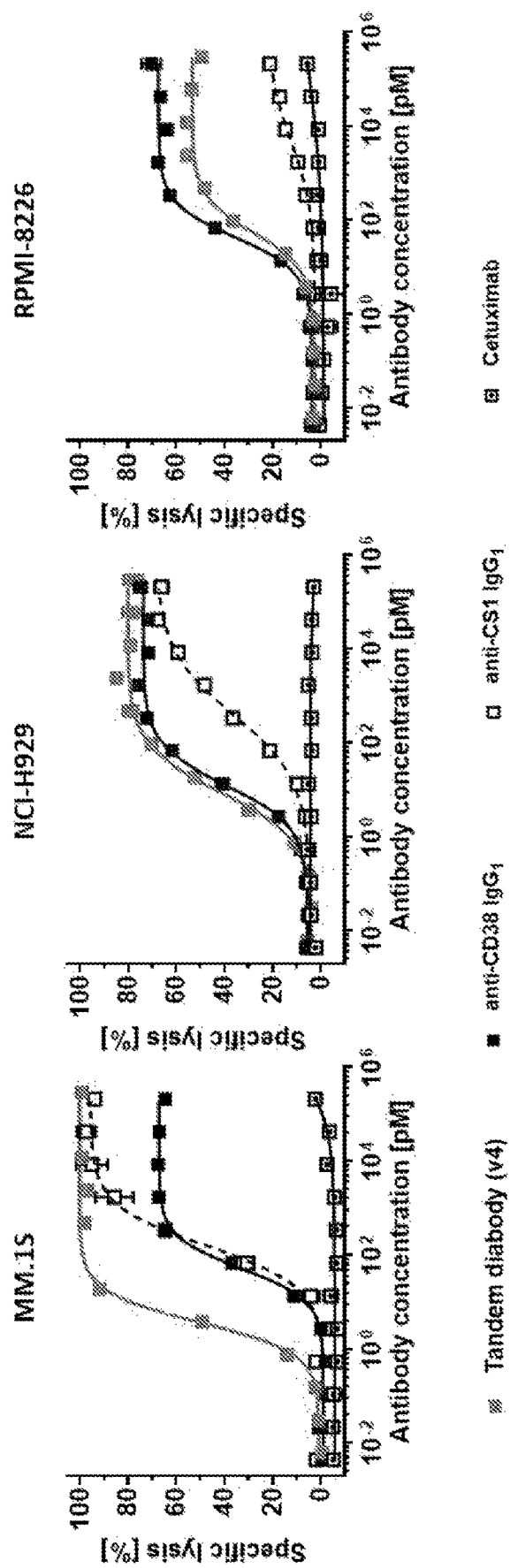
Figure 11:
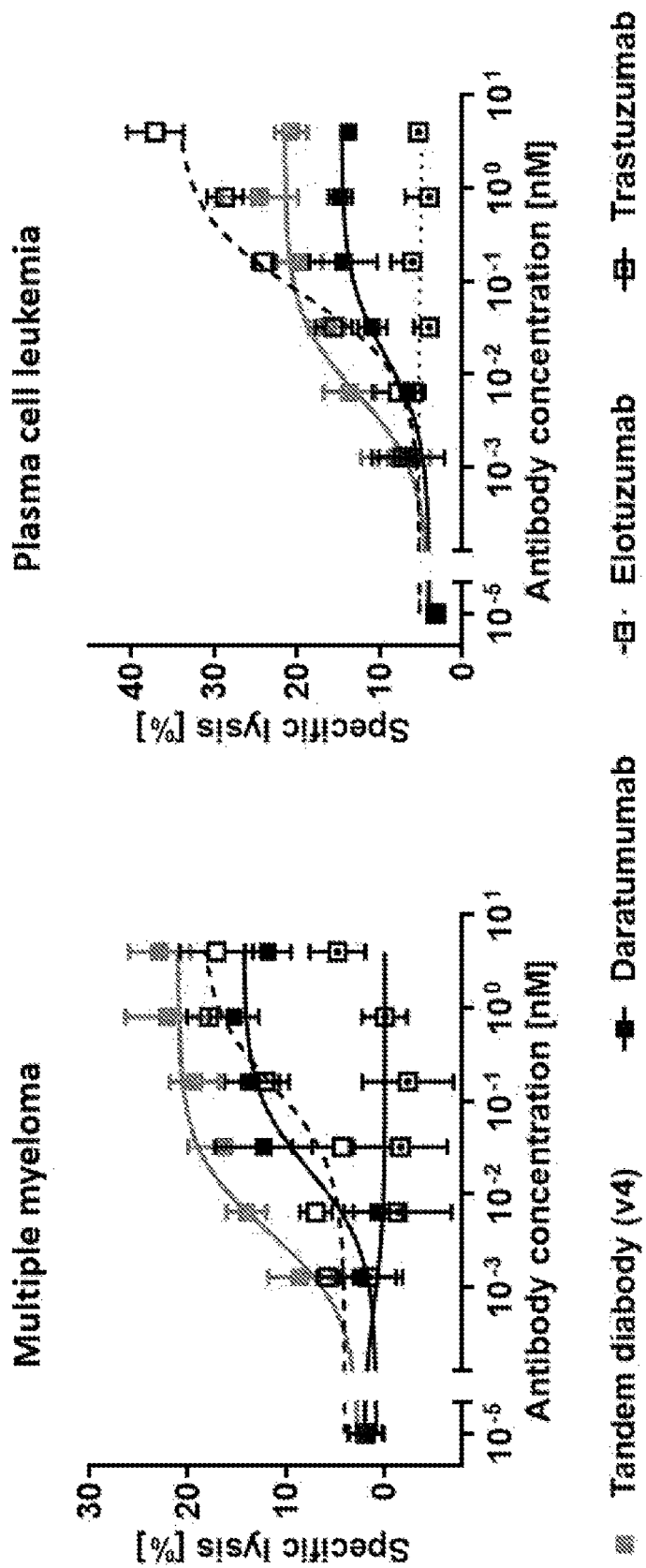

FIG. 3 shows increased binding affinity of tandem diabody binding to primary human NK-cells in presence and absence of polyclonal human IgG compared with anti-CD16A scFv FIG. 4 shows tandem diabody and anti-CD16A scFv binding to primary human NK-cells FIG. 5 shows surface retention of tandem diabody on primary human NK-cells in presence and absence of polyclonal human IgG FIG. 6 shows tandem diabody-induced NK-cell-mediated cytotoxicity towards BCMA$^+$ myeloma cell lines in vitro in presence and absence of polyclonal human IgG FIG. 7 shows NK-cell-NK-cell lysis is induced by variant 2 but not variant 4 tandem diabody FIG. 8 shows NK-cell-NK-cell lysis is induced by bivalent, monospecific anti-CD16A diabody but not monovalent anti-CD16A scFv FIG. 9 shows antibody-induced cytokine release in human PBMC cultures in presence and absence of BCMA+ target cells FIG. 10 shows in vitro cytotoxicity of primary human NK-cells towards BCMA+ target cell lines in presence of increasing concentrations of BCMA/CD16A-directed tandem diabody and comparator antibodies FIG. 11 shows in vitro cytotoxicity of primary human NK-cells towards primary myeloma cells in presence of increasing concentrations of BCMA/CD16A-directed tandem diabody and comparator antibodies.

Figure 12:
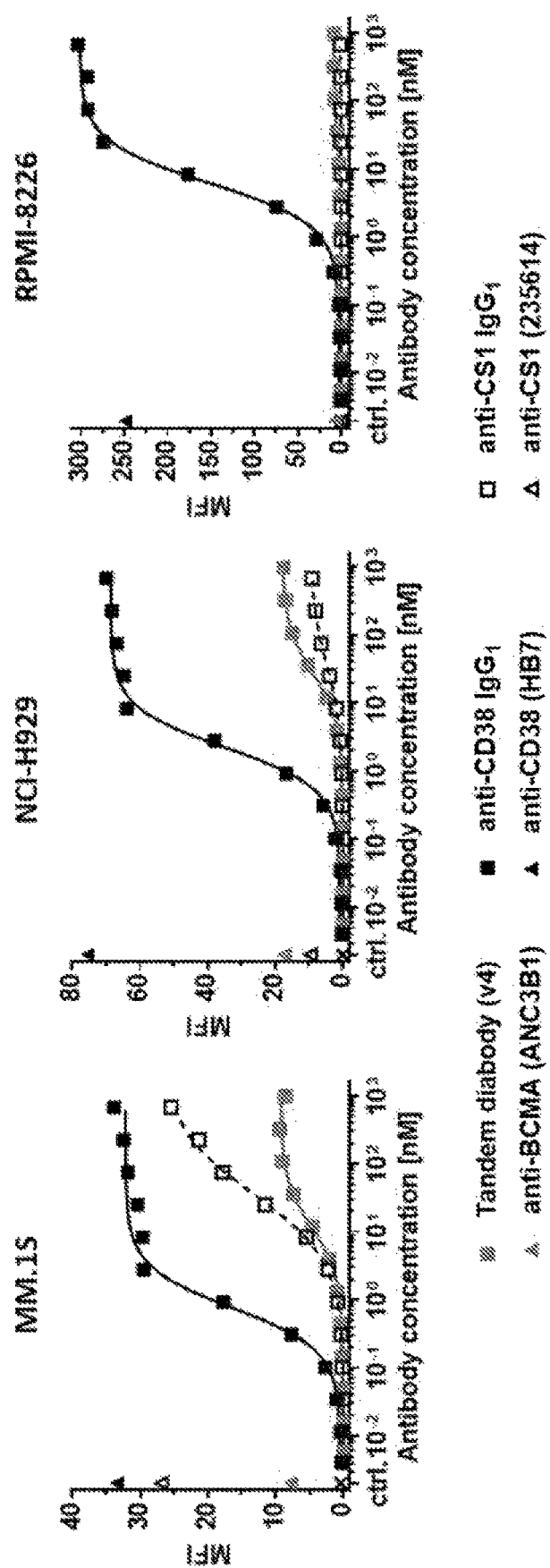

FIG. 12 shows antibody binding to myeloma cell lines

Figure 13:
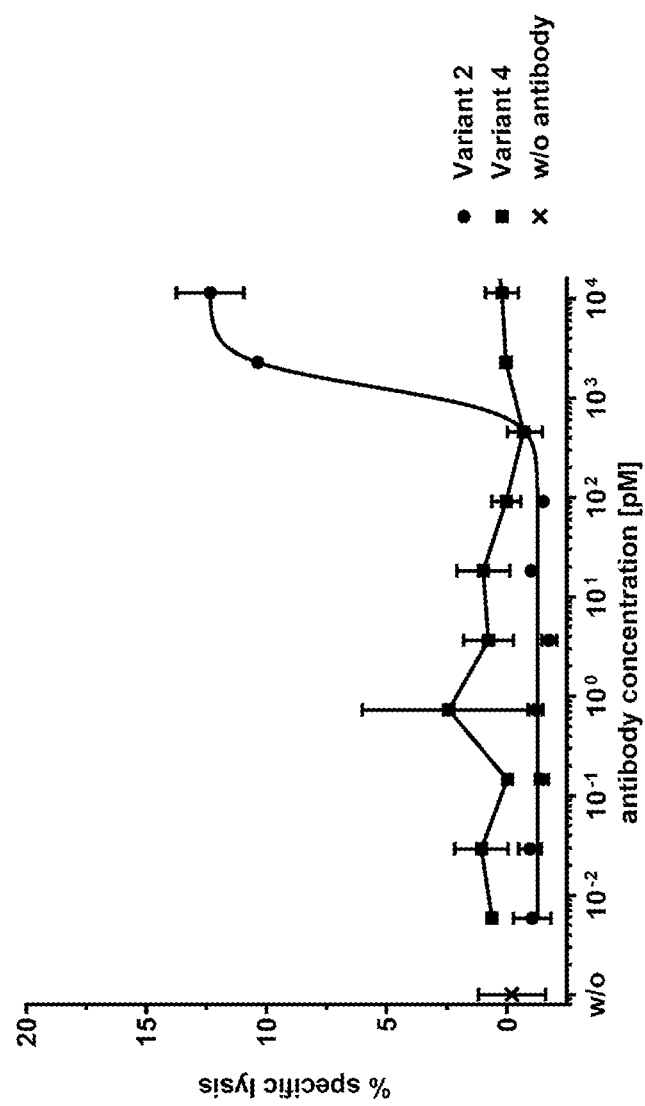

FIG. 13 4 h calcein-release cytotoxicity assay with HLA-A2$^{MMP1-003}$/CD16A tandem diabody variant 2 and variant 4 to assess antibody-induced NK-NK cell lysis.

DETAILED DESCRIPTION OF THE INVENTION

Therefore, the invention provides a multispecific antigen-binding molecule comprising at least four antigen-binding sites put together in a chain, wherein at least two juxtaposed antigen-binding sites have specificity for CD16A and at least one further antigen-binding site having specificity for a target cell antigen is positioned outside of the pair of two juxtaposed antigen-sites having specificity for CD16A.

Hence, the invention provides a multispecific antigen-binding molecule comprising at least four antigen-binding sites. The antigen-binding sites may be non-covalently associated with each other or covalently bound with one another. If the antigen-binding sites are covalently bound with one another they may be fused with each other by a peptide bond or a peptide linker. Alternatively, the antigen-binding sites may be linked by a chemical conjugation such as a disulfide bridge, e.g. between a cysteine residue of at least one antigen-binding site and a cysteine residue of another antigen-binding site, ester linkage or by chemical crosslinking.

In embodiments where the antigen-binding sites are bound with each other by a peptide bond or a peptide linker the antigen-binding molecule may be a monomer consisting of a single polypeptide chain or the antigen-binding molecule may be a multimer comprising at least two polypeptide chains, i.e. two, three or more polypeptide chains, which are covalently or non-covalently associated with one another.

In certain embodiments the antigen-binding molecule comprising at least four antigen-binding sites is a dimeric molecule consisting of two polypeptide chains non-covalently associated with each other, wherein each polypeptide chain comprises at least four variable domains. An example of such a dimeric antigen-binding molecule is a tandem diabody further described below.

In certain embodiments the antigen-binding molecule does not comprise a constant antibody domain.

The invention provides a multispecific antigen-binding molecule comprising antigen-binding sites specifically binding to CD16A for engaging a NK-cell and a target antigen (TA) different from CD16A, wherein the antigen-binding molecule consists of two polypeptide chains. An example for such an antigen-binding molecule is a tandem diabody.

The term "binding protein" refers to an immunoglobulin derivative with antigen binding properties; i.e. the binding protein is an antigen binding protein. The binding protein comprises an immunologically functional immunoglobulin portion capable of binding to a target antigen. The immunologically functional immunoglobulin portion may comprise immunoglobulins, or portions thereof, fusion peptides derived from immunoglobulin portions or conjugates combining immunoglobulin portions that form an antigen binding site. The binding protein comprises at least one antigen binding site which is the region, portion or domain of the binding protein that binds to the target antigen. Each antigen binding site comprises at least the CDRs of the immunoglobulin heavy or light chains from which the antigen binding site was derived.

The term "binding protein" refers also to antibody fragments, antibody derivatives or antibody-like binding proteins that retain specificity and affinity for their antigen including, for example, IgG-like or non-IgG-like fusion peptides based on Fv domains either without or with additional constant domains, e.g. Fc-scFv, Fab, Fab', F(ab')$_2$, Fv fragments, single-chain Fv, tandem single-chain Fv ((scFv)$_2$), Bi-specific T-cell engagers (BiTE®) or Bi-specific NK-cell engagers (BiKE), dual affinity retargeting antibodies (DART™), diabody, single-chain diabody and tandem diabody (TandAb®); triabody, tribody or Tri-specific NK-cell engagers (TriKE). Dependent on desired features, such as valency, multispecificity, pharmacokinetic and pharmacodynamic properties Fv and/or constant domains and/or additional functional domains may be modularly assembled in different formats or scaffolds, such that, for example, described in Brinkmann and Kontermann, mAbs, 2017, 9(2):182-192 or in Spiess et al., 2015, Molecular Immunology, 67:95-106.

The term "antigen-binding site" refers to an antibody-antigen combining site or paratope of the antigen-binding molecule that binds, in particular specifically, to an antigenic determinant (epitope) of an antigen. The antigen-binding site is the binding portion of the antigen-binding molecule which is capable of recognizing the antigen and binds specifically to the antigen. The antigen-binding site comprises the variable domains of both the light (VL) and heavy (VH) chains that combine with the antigen, i.e. bind to the epitope of the antigen. In certain embodiments the antigen-binding site may be a single domain (sdAb), e.g. V$_H$H fragments from camelids or V$_{NAR}$ fragments from cartilaginous fishes.

Each antigen-binding site is formed by an antibody, i.e. immunoglobulin, variable heavy chain domain (VH) and an antibody variable light chain domain (VL) binding to the same epitope, whereas the variable heavy chain domain (VH) comprises three heavy chain complementarity determining regions (CDR): HCDR1, HCDR2 and HCDR3; and the variable light chain domain (VL) comprises three light chain complementary determining regions (CDR): LCDR1, LCDR2 and LCDR3. In certain embodiments of the invention the binding protein is devoid of immunoglobulin constant domains. The variable heavy and light chain domains of an antigen-binding site may be covalently linked with one another, e.g. by a peptide linker, or non-covalently associate with one another to form an antigen-binding site.

The term "polypeptide chain" refers to a polymer of amino acid residues linked by amide bonds. The polypeptide chain is, preferably, a single chain fusion protein which is not branched. In the polypeptide chain the variable domains are linked one after another by a peptide linker or a peptide bond from the N-terminus to the C-terminus of the polypeptide. The polypeptide chain may have contiguous amino acid residues in addition to the variable domains and peptide linkers linking the variable domains N-terminally and/or C-terminally. For example, the polypeptide chain may contain a Tag sequence, preferably at the C-terminus which might be useful for the purification of the polypeptide. An example of a Tag sequence is a His-Tag, e.g. a His-Tag consisting of six histidine-residues.

In some embodiments the antigen-binding molecule consists of a single polypeptide chain. Such an antigen-binding molecule is a monomer. In other embodiments the antigen-binding molecule comprises at least two polypeptide chains. Such an antigen-binding molecule is a multimer, e.g. dimer, trimer or tetramer.

In certain embodiments the antigen-binding molecule is a homodimer and consists of two identical polypeptide chains.

Such a homodimer is the dimeric and bispecific tandem diabody.

The term "tandem diabody" refers to an antigen-binding molecule constructed by linking at least four variable domains (two heavy chain variable domains (VH) and two light chain variable domains (VL)) in a single gene construct enabling homo-dimerization. In such tandem diabodies the linker length is such that it prevents intramolecular pairing of the variable domains so that the molecule cannot fold back upon itself to form a monomeric single-chain molecule, but rather is forced to pair with the complementary domains of another chain. The variable domains are also arranged such that the corresponding variable domains pair during this dimerization (Weichel et al., 2015, European Pharmaceutical Review, 20(1):27-32).

Following expression from the single gene construct, two identical polypeptide chains fold head-to-tail forming a functional non-covalent homodimer of approximately 105 kDa. Despite the absence of intermolecular covalent bonds, the homodimer is highly stable once formed, remains intact and does not revert back to the monomeric form. Tandem diabodies have a number of properties that provide advantages over traditional monoclonal antibodies and other smaller bispecific molecules. Tandem diabodies contain only antibody variable domains and therefore are contemplated to lack side effects or non-specific interactions that may be associated with an Fc moiety. For example, Fc receptors which can bind to Fc regions are found on numerous cell types such as white blood cells (e.g., basophils, B-cells, eosinophils, NK-cells, neutrophils and the like) or Kupffer cells. Because tandem diabodies allow for bivalent binding to CD16A and the target cell antigen, the avidity is the same as that of an IgG. The size of a tandem diabody, at approximately 105 kDa, is smaller than that of an IgG, but is well above the threshold for first-pass renal clearance, offering a pharmacokinetic advantage compared with smaller bispecific formats based on antibody-binding domains or non-antibody scaffolds. Moreover, tandem diabodies are advantageous over other bispecific binding proteins such as BiTE® or DART™ molecules based on these pharmacokinetic and avidity properties resulting in longer intrinsic half-lives and enhanced cytotoxicity. Tandem diabodies are well expressed in host cells, for example, mammalian CHO cells. It is contemplated that robust upstream and downstream manufacturing process is available for tandem diabodies.

The term "multispecific" refers to an antigen-binding molecule, comprising antigen-binding sites that bind to at least two different epitopes, in particular epitopes of different antigens. "Multispecific" includes, but is not limited to, bispecific, trispecific and tetraspecific.

The term "target antigen" refers to an antigen which is expressed by or associated with a type of cell, i.e. target cell, or virus to which the NK-cells should be directed to induce or trigger the NK-cell cytotoxicity. Examples of a target antigen may be tumor antigen or tumor-associated antigen (TAA). The tumor antigen or TAA may be expressed on the surface of the target cell or displayed by a MHC complex as a MHC-restricted peptide. Examples of tumor antigens include but are not limited to CD5, CD19, CD20, CD30, CD33, CD38, CD138, CS-1, matrix metalloproteinase 1 (MMP1), the laminin receptor precursor protein, BCMA, Ep-CAM, PLAP, Thomsen-Friedenreich (TF) antigen, MUC-1 (mucin), IGFR, IL4-R alpha, IL13-R, HER2/neu, HER3, PSMA, CEA, TAG-72, HPV E6, HPV E7, BING-4, 9D7, EphA2, EphA3, Telomerase, Mesothelin, SAP-1, Survivin, Cancer Testis antigens (BAGE family, CAGE family, GAGE family, MAGE family, SAGE family, XAGE family), NY-ESO-1/LAGE-1, PRAME, SSX-2, Melan-A/MART-1, Gp100/pmel17, Tyrosinase, TRP-1/-2, MC1R, ß-catenin, BRCA1/2, CDK4, CML66, MART-2, p53, Ras, TGF-ßRII and TCR (from Categories of Tumor Antigens, Holland-Frei Cancer Medicine. $6^{th}$ edition. Kufe D W, Pollock R E, Weichselbaum R R. et al., editors Hamilton (ON):Becker; 2003). In certain embodiments of the invention the target antigen is not EGFR or EGFRvIII.

In other embodiments the target antigen may be an infectious agent such as viral or bacterial pathogens, for example from a dengue virus, herpes simplex, influenza virus or HIV. In certain embodiments the target antigen is not EGFR or EGFRvIII.

In some embodiments the invention provides a multispecific antigen-binding molecule, e.g. tandem diabody, comprising antigen-binding sites specifically binding to CD16A and a target antigen (TA) different from CD16A, wherein the antigen-binding molecule consists of two polypeptide chains. Each polypeptide chain comprises at least four variable domains from the group consisting of (i) a heavy chain variable domain specific for CD16A (VH_CD16A),
(ii) a light chain variable domain specific for CD16A (VL_CD16A),
(iii) a heavy chain variable domain specific for the target antigen (VH_TA), and
(iv) a light chain variable domain specific for the target antigen (VL_TA).

Figure 1:
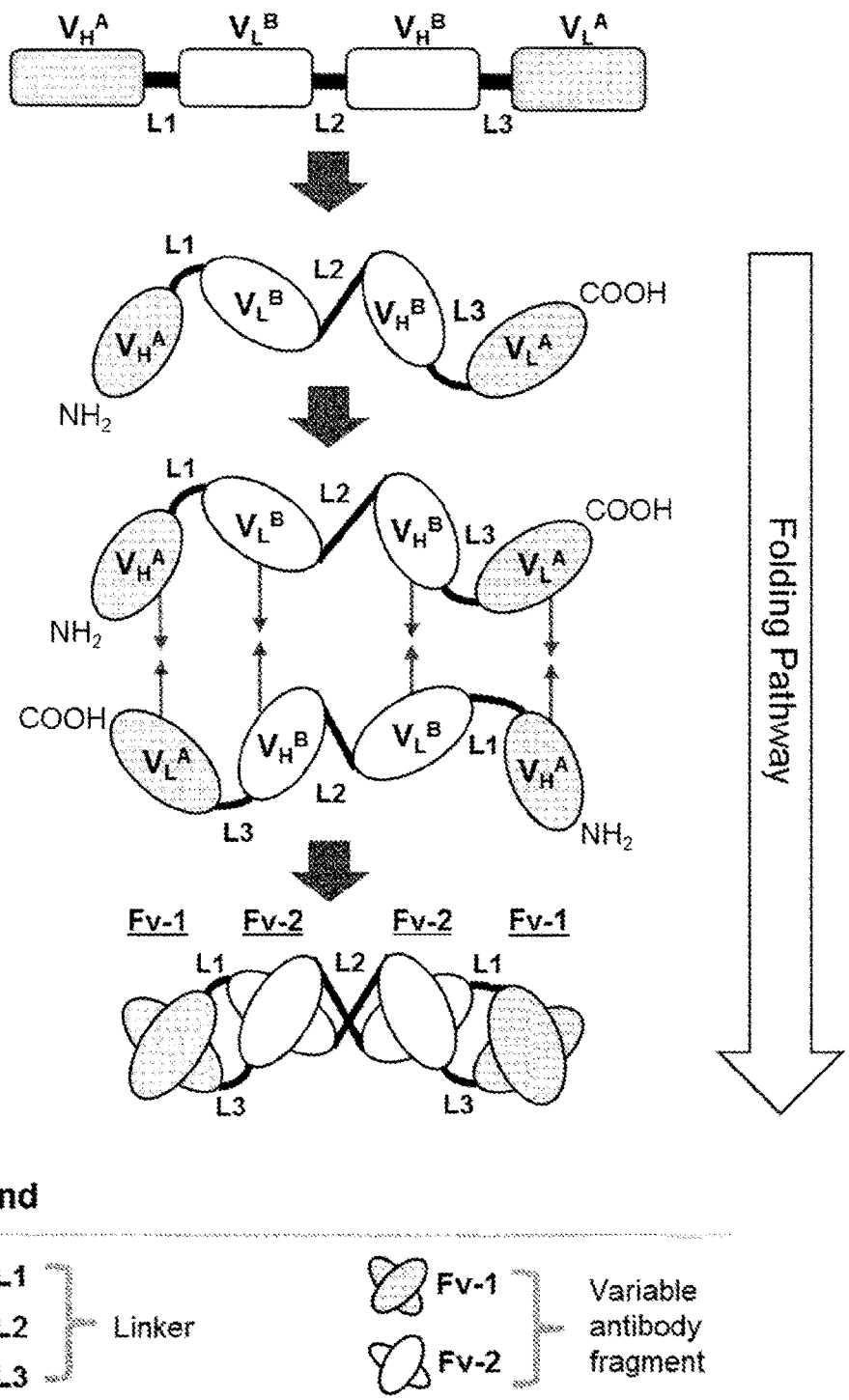
FIG. 1 Schematic representation of gene and domain organization of a multispecific tandem diabody specifically binding to a first antigen A (e.g. BCMA) and a second antigen B (CD16A). Tandem diabodies are expressed as a single polypeptide comprised of four variable domains connected via short linkers L1, L2 and L3. Following expression, two monomeric polypeptides associate non-covalently head-to-tail to form the functional homodimeric tandem diabody providing four antigen-binding sites (Fv-1, Fv-2). L1, L2, L3: Peptide Linker; VH: heavy chain variable domain; VL: light chain variable domain. A, B: antigen specificity.
Figure 2:
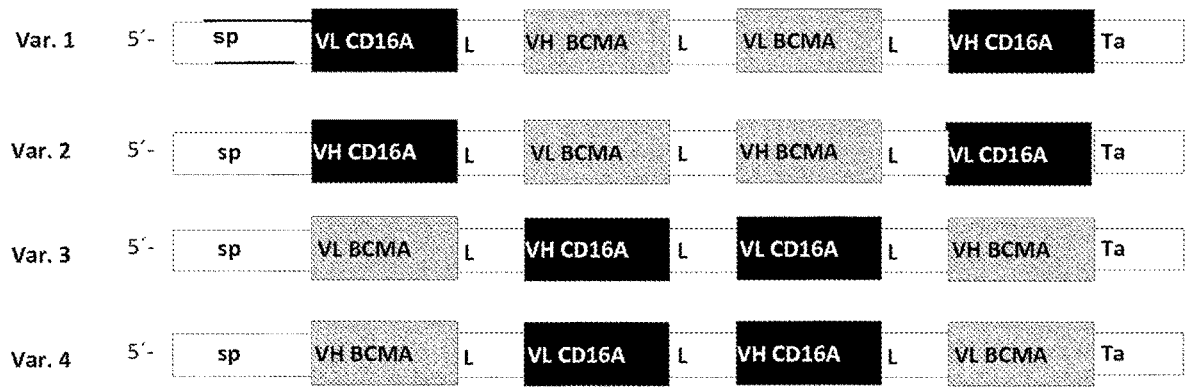
FIG. 2 Schematic representation of gene organization and domain order in polypeptides of multispecific tandem diabody specifically binding to BCMA and CD16A. Tandem diabodies are expressed as a single polypeptide comprised of four variable domains connected via short linkers L1, L2 and L3. First line: var. 1=variant 1, second line: var. 2=variant 2, third line: var.3=variant 3 and fourth line: var.4=variant 4.

These variable domains are positioned within each of the two polypeptide chains from the N-terminus to the C-terminus of the polypeptide in the order:
VH_TA-VL_CD16A-VH_CD16A-VL_TA (FIG. 1)

In alternative embodiments the variable domains may be positioned within each of the two polypeptide chains from the N-terminus to the C-terminus of the polypeptide in the order:VL_TA-VH_CD16A-VL_CD16A-VH_TA.

Hence, the heavy and light chain variable domains of anti-CD16A are positioned as a pair of juxtaposed domains in the center, inside of the polypeptide chain, while the heavy and light chain variable domains specifically binding to the target antigen are positioned N-terminally and C-terminally to the pair of juxtaposed anti-CD16A domains within the polypeptide.

Advantageously, such variable domain arrangement in the polypeptide chain prevents an induction of NK-cell lysis by NK-cells through cross-linking of CD16A receptors on a NK-cell by the antigen-binding molecule, because the pair of two juxtaposed CD16A antigen-binding sites inside the antigen-binding molecule is not capable of cross-linking CD16A receptors that are not expressed on the same cell. However, on the other side the two CD16A antigen-binding sites of the antigen-binding molecule are able to bivalently bind to CD16A expressed on the same NK-cell, thereby increasing the cytotoxic potency of the NK-cell activation through increased avidity.

Such multispecific antigen-binding molecule, e.g. tandem diabody, is bispecific and at least tetravalent, i.e. comprises at least four antigen-binding sites.

In a further embodiment the at least four variable domains are linked by peptide linkers L1, L2 and L3 and are positioned from the N- to the C-terminus of the polypeptide chain in the order: VH_TA-L1-VL_CD16A-L2-VH_CD16A-L3-VL_TA (FIG. 1).

In other embodiments the variable domains and peptide linkers are positioned from the N- to the C-terminus of the polypeptide chain in the order: VL_TA-L1-VH_CD16A-L2-VL_CD16A-L3-VH_TA.

The length of the linkers influences the flexibility of such multispecific antigen-binding molecule according to reported studies. Accordingly, in some embodiments, the length of the peptide linkers L1, L2 and L3 is such that the domains of one polypeptide can associate intermolecularly with the domains of another polypeptide to form a tandem diabody. In certain embodiments, such linkers are "short", i.e. consist of 0, 1, 2, 3, 4, 5, 6, 7, 8, 9, 10, 11 or 12 amino acid residues. Thus, in certain instances, the linkers consist of about 12 or less amino acid residues, for example 3-12, 3-10, or 3-9 amino acid residues. In the case of 0 amino acid residues, the linker is a peptide bond. Such short linkers favor the intermolecular dimerization of the two polypeptides by binding and forming correct antigen-binding sites between antibody variable light chain domains and antibody variable heavy chain domains of different polypeptides. Shortening the linker to about 12 or less amino acid residues generally prevents adjacent domains of the same polypeptide chain from intramolecular interaction with each other. In some embodiments, these linkers consist of about 3 to about 12, for example 3, 4, 5 or 6 contiguous amino acid residues.

The linkers L1, L2 and L3 may consist of the same number of amino acid residues or the polypeptide chain may comprise linkers of different length. While shorter central linkers L2 of 3 to 9, preferably 3 to 6, most preferably of 3 amino acid residues are in some embodiments favorable for increasing the affinity of bivalent CD16A binding on NK cells, more flexible linkers L1 and L3 of 9 to 12, preferably 12 amino acid residues can be favorable for potent cross linking of the NK cell with the target cell in some embodiments. In one embodiment the central linker L2 joining the VH and VL domain specific for CD16A consists of less amino acid residues than the outer linkers L1 and L3 joining the variable target binding domains with the VH or VL domains specific CD16A. In such embodiments the central linker L2 may consist of 3 to 9, for example 3 to 6, amino acid residues. In some embodiments the central linker L2 consists of 3 amino acid residues and the linkers L1 and L3 consist of 4, 5, 6, 7, 8, 9, 10, 11 or 12 amino acid residues, for example 6 to 9 or 6 to 12 amino acid residues. In particular embodiments the central linker L2 consists of 3 amino acid residues and the linkers L1 and L3 consist of 6, 9 or 12 amino acid residues. In other embodiments the central linker L2 consists of 6 amino acid residues and the linkers L1 and L3 consist of 7, 8, 9, 10, 11 or 12 amino acid residues, for example 9 to 12 amino acid residues. In particular embodiments the central linker L2 consists of 3 amino acid residues and the linkers L1 and L3 consist of 9 or 12 amino acid residues. In further embodiments the central linker L2 consists of 9 amino acid residues and the linkers L1 and L3 consist of 10, 11 or 12 amino acid residues.

Regarding the amino acid composition of the linkers, peptides are selected that do not interfere with the dimerization of the two polypeptides. For example, linkers comprising glycine and serine residues generally provide protease resistance. The amino acid sequence of the linkers can be optimized, for example, by phage display methods to improve the antigen binding and production yield of the antigen-binding polypeptide dimer. In some embodiments $(G_2S)_x$ peptide linkers are used, e.g. $(G_2S)$, $(G_2S)_2$, $(G_2S)_3$, $(G_2S)_4$, $(G_2S)_5$, $(G_2S)_6$, $(G_2S)_7$ or Examples of peptide linkers suitable for a tandem diabody in some embodiments are GGS, GGSG (SEQ ID NO:13), GGSGG (SEQ ID NO:14), GGSGGS (SEQ ID NO:15) or GGSGGSGGS (SEQ ID NO:16). In a particular embodiment linkers L1 and L3 are $(G_2S)_4$ and linker L2 is $(G_2S)$.

In certain embodiments the target antigen is an antigen displayed on a myeloma cell or plasma cell. Antigens expressed on myeloma cells are reviewed by Sherbenou et al. (Blood Rev 2015, 28(2), 81-91). Examples of antigens expressed on a myeloma cell or plasma cell are BCMA, CD138, CD38, CS-1, CD19 and CD20. Preferably, the antigen-binding molecule binds to the extracellular domains of the antigen.

"Myeloma cell" is a malignant (cancerous) plasma cell arising from a plasma cell in the bone marrow. In myeloma, malignant plasma cells produce large amounts of abnormal antibodies that lack the capability to fight infection. These abnormal antibodies are the monoclonal protein, or M-protein, that functions as a tumor marker for myeloma. The myeloma cell has the phenotype $CD19^-/CD38^+/CD138^+/BCMA^+$. Hence, CD38, CD138 and BCMA represent antigens expressed on a myeloma cell.

B-cell maturation antigen (BCMA, CD269 or TNFRSF17) is a protein of the TNF receptor superfamily which is crucial for long term survival of plasma cells through its binding of B-cell activating (BAFF) and A proliferation-inducing ligand (APRIL) (O'Connor, B. P. et al. BCMA is essential for the survival of long-lived bone marrow plasma cells. J. Exp. Med. 2004, 199, 91-96). Human BCMA is a 184 amino acid (aa) protein consisting of a 54 aa extracellular domain, a 23 aa transmembrane domain, and a 107 aa intracellular domain (Entrez Gene IDs: 608 (Human) 102145399 (Cynomolgous Monkey); UniProt Q02223 (Human)).

In certain embodiments the antigen-binding molecule employs antibodies specifically binding to the extracellular domain of BCMA.

Preferably, such anti-BCMA Fv antibody employed in the antigen binding molecule of the invention interacts with BCMA with an equilibrium dissociation constant ($K_D$) (measured by Biacore) of less than $10^{-7}$ M, preferably less than $10^{-8}$ M, most preferably less than $10^{-10}$ M. Such anti-BCMA variable (Fv) domains incorporated in the antigen binding molecule of the invention are capable of redirecting CD16A engaged NK cells and inducing ADCC in the presence of $BCMA^+$ MM cells. Proof-of-concept for bispecific antibodies engaging T cells via CD3 towards $BCMA^+$ myeloma cells in vitro and in vivo has been reported (e.g., Hipp S. et al., Leukemia. 2017 August; 31(8):1743-1751. Epub 2016 Dec. 27)

Such antibodies are obtainable, for example, by phage or ribosome library screening methods or immunization of a non-human animal with the extracellular domain of BCMA as described, for example, in Ryan M. C, et al., Antibody targeting of B-cell maturation antigen on malignant plasma cells. Mol Cancer Ther. 2007, 6, 3009-3018.

Ryan et al. describes the production of anti-BCMA antibodies with cytotoxic activity either as IgG or antibody drug conjugates. Ryan M. C, et al., which is incorporated by reference, describes the generation of human BCMA-selective antibodies for tumor cell targeting. The antibodies were generated against the human BCMA extracellular domain (ECD, amino acids 5-51; NP_001183). The antibody induced potent ADCC towards MM cells in vitro which was increased with Fc mutations that enhance CD16A binding. The binding affinity $K_D$ of SG1 towards H929 cells was 51 nmol/L by saturation binding. These antibodies demonstrated in vitro antitumor activity against MM cell lines and their and, thus, their Fv-domain can be employed as BCMA antigen binding sites in the antigen binding molecule according to the invention.

Further, WO 02/066516 describes BCMA antibodies cross-reactive with TACI. Anti-BCMA/TACI bispecific antibodies are described binding of residues 1-48 of BCMA and residues 30-67 and 68-154 of TACI. The variable heavy and light chain domains thereof could be employed in the antigen binding molecule of the invention and are incorporated by reference.

Ramadoss et al., J. Am. Chem. Soc. 2015, 137, 5288-5291, incorporated by reference, describes a bispecific (Bi-Fab-BCMA) antibody which redirects T cells to lyse malignant MM cells. It is described that bispecific antibodies can be useful for the treatment of MM, as they target quiescent cancer stem cells as well as with low numbers of tumor-associated antigens.

WO 2014/122144 describes a bispecific antibody specifically binding to human BCMA and CD3 in a bispecific format. The disclosed anti-BCMA variable domains are suitable for the antigen binding molecule of the invention.

WO 2013/072406 discloses anti-BCMA Fv domains designated as BCMA-1 to BCMA-108 in bispecific single-chain antibodies having a second specificity for CD3 for engaging T cells. Anti tumor efficacy of these BCMA/CD3 bispecific single chain antibodies in human tumor xenograft model is described and, thus, these anti-BCMA Fv domains can be employed in the antigen-binding molecule of the invention.

Further anti-BCMA antibodies that can be employed in bispecific antibodies engaging immune effector cells such as T- or NK-cells have been disclosed in, WO 2010/104949, WO 2012/163805, WO 2013/072415, WO 2014/140248, and WO 2014/068079. Also these references describe anti-BCMA Fv-domains specifically targeting BCMA with high affinity and bispecific antibodies employing such anti-BCMA Fv-domains which induce potent and efficacious myeloma cell lysis. Therefore, proof-of-concept has been shown for anti-BCMA Fv-domains in bispecific antibodies for redirecting T cell to lyse MM cells. The tandem diabody also potently engages immune effector cells like T- or NK cells to kill tumor cells (Weichel et al., 2015). Therefore, these anti-BCMA Fv domains of the art may be employed in the tandem diabody of the invention and the novel Fv domain protein conformation comprising the two CD16A domains according to the invention will induce an enhanced NK cell cytotoxicity towards MM cells.

A further starget is CD138 that is ubiquitously expressed on myeloma and normal plasma cells (Pellat-Deceunynck C., et al. Expression of CD28 and CD40 in human myeloma cells: a comparative study with normal plasma cells. Blood. 1994, 84(8):2597-603). An example of an anti-CD138 antibody is Indatuximab (Biotest) (Jagannath S, et al. BT062 an antibody-drug conjugate directed against CD138, shows clinical activity in patients with relapsed or relapsed/refractory multiple myeloma (Blood 2011, 118(21) (Abstract 305)).

Furthermore, CD38 (cyclic ADP ribose hydrolase) is expressed on nearly all plasma cells and myeloma cells. Examples of an anti-CD38 antibody are daratumumab (Genmab, Janssen) (De Weers M et al. Daratumumab, a novel therapeutic human CD38 monoclonal antibody, induces killing of multiple myeloma and other hematological tumors. J. Immunol. 2011, 186(3):1840-8) and isatuximab (Sanofi) (Deckert J., et al. SAR650984, a novel humanized CD38-targeting antibody, demonstrates potent antitumor activity in models of multiple myeloma and other CD38+ hematological malignancies. Clin. Cancer Res. 2014, 20(17):4574-83).

Further antigen-binding sites and variable domains of antigen-binding sites that bind to antigens expressed on myeloma cells, in particular BCMA can be derived from other known or commercially available antibodies or generated de novo by methods well known in the art. For example, variable domain antigen-binding sites that bind to BCMA can be obtained by selecting variable fragments (Fvs) that are specific for BCMA. This can be accomplished, for example, by screening single-chain Fv (scFv) phage display libraries or through hybridoma technology. For instance, IgM-based phage display libraries of human scFv sequences can be subjected to several rounds of in vitro selection to enrich for binders specific to the BCMA (Example 1). Affinities of selected scFvs may be further increased by affinity maturation.

Thus, the invention further provides a multispecific antigen-binding molecule, e.g. tandem diabody, comprising antigen-binding sites specifically binding to CD16A and a target antigen (TA) expressed on myeloma cells or plasma cells, wherein the antigen-binding molecule consists of two polypeptide chains. Each polypeptide chain comprises at least four variable domains from the group consisting of (i) a heavy chain variable domain specific for CD16A (VH_CD16A),
(ii) a light chain variable domain specific for CD16A (VL_CD16A),
(iii) a heavy chain variable domain specific for the target antigen (VH_TA) expressed on a myeloma cell or plasma cell, and
(iv) a light chain variable domain specific for the target antigen (VL_TA) expressed on a myeloma cell or plasma cell; wherein the target antigen expressed on a myeloma cell or plasma cell is selected from the group consisting of BCMA, CD138, CD38, CS-1, CD19 and CD20; preferably from the group consisting of BCMA, CD138 or CD38.

The variable domains are positioned within each of the two polypeptide chains from the N-terminus to the C-terminus of the polypeptide in the order: VH_TA-VL_CD16A-VH_CD16A-VL_TA (FIG. 1)

A further embodiment is a multispecific antigen-binding molecule comprising antigen-binding sites specifically binding to CD16A and BCMA, wherein the antigen-binding molecule consists of two polypeptide chains. Each polypeptide chain comprises at least four variable domains from the group consisting of (i) a heavy chain variable domain specific for CD16A (VH_CD16A),
(ii) a light chain variable domain specific for CD16A (VL_CD16A),
(iii) a heavy chain variable domain specific for BCMA, and
(iv) a light chain variable domain specific for BCMA.

These variable domains are positioned within each of the two polypeptide chains from the N-terminus to the C-terminus of the polypeptide in the order: VH_BCMA-VL_CD16A-VH_CD16A-VL_BCMA (FIG. 1).

Alternatively, the domains may be positioned in the order: VL_BCMA-VH_CD16A-VL_CD16A-VH_BCMA.

The multispecific antigen-binding molecule, e.g. tandem diabody, comprises antigen-binding sites binding to CD16A.

Preferably, the multispecific antigen-binding molecule binds to CD16A, but not to CD16B. An antigen-binding site comprising heavy and light chain variable domains binding to CD16A, but not binding to CD16B may be provided by an antigen-binding site which specifically binds to an epitope of CD16A which comprises amino acid residues of the C-terminal sequence SFFPPGYQ (SEQ ID NO:11) and/or residues G130 and/or Y141 of CD16A (SEQ ID NO:20) which are not present in CD16B.

In some embodiments the multispecific antigen-binding molecule comprises a heavy and a light variable chain domain specific for CD16A, wherein (i) the heavy chain variable domain specific for CD16A (VH_CD16A) comprises a heavy chain CDR1 having the amino acid sequence set forth in SEQ ID NO:1; a heavy chain CDR2 having the amino acid sequence set forth in SEQ ID NO:2; a heavy chain CDR3 having the amino acid sequence set forth in SEQ ID NO:3 and the light chain variable domain specific for CD16A comprises a light chain CDR1 having an amino acid sequence set forth in SEQ ID NO:4; a light chain CDR2 having an amino acid sequence set forth in SEQ ID NO:5; and a light chain CDR3 having an amino acid sequence set forth in SEQ ID NOs:6; or
  (ii) the heavy chain variable domain specific for CD16A (VH_CD16A) has an amino acid sequence set forth in SEQ ID NOs:8; and/or
  (iii) the light chain variable domain specific for CD16A (VL_CD16A) has the amino acid sequence set forth in SEQ ID NO:9.

This affinity maturated anti-CD16A domain does not bind to CD16B and recognizes the known CD16A allotypes F158 and V158 with similar affinity. Two allelic single nucleotide polymorphisms have been identified in human CD16A altering the amino acid in position 158, which is important for interaction with the hinge region of IgGs. The allelic frequencies of the homozygous 158 F/F and the heterozygous 158 V/F alleles are similar within the Caucasian population, ranging between 35 and 52% or 38 and 50%, whereas the homozygous 158 V/V allele is only found in 10-15% (Lopez-Escamez J A et al.; BMC Med Genet 2011; 12:2.). Activating of NK cells by this anti-CD16A domain in all patients due to the similar affinity is advantageous.

In an alternative embodiment (i) the heavy chain CDR2 may be replaced by a heavy chain CDR2 having the amino acid sequence set forth in SEQ ID NO:7 or (ii) the heavy chain variable domain may be replaced by a heavy chain variable domain having the amino acid sequence set forth in SEQ ID NO:10.

Further CD16A antigen-binding sites comprising heavy and light variable chain domains that bind to CD16A, but not to CD16B are described in WO 2006/125668.

In a particular embodiment the invention is a multispecific antigen-binding molecule comprising antigen-binding sites specifically binding to CD16A and BCMA, wherein the antigen-binding molecule consists of two polypeptide chains. Each polypeptide chain comprises at least four variable domains from the group consisting of
  (i) a heavy chain variable domain specific for CD16A (VH_CD16A) comprising a heavy chain CDR1 having the amino acid sequence set forth in SEQ ID NO:1; a heavy chain CDR2 having the amino acid sequence set forth in SEQ ID NO:2; a heavy chain CDR3 having the amino acid sequence set forth in SEQ ID NO:3,
  (ii) a light chain variable domain specific for CD16A (VL_CD16A) comprising a light chain CDR1 having an amino acid sequence set forth in SEQ ID NO:4; a light chain CDR2 having an amino acid sequence set forth in SEQ ID NO:5; and a light chain CDR3 having an amino acid sequence set forth in SEQ ID NO: 6,
  (iii) a heavy chain variable domain specific for BCMA and (iv) a light chain variable domain specific for the target cell antigen BCMA,
  wherein these variable domains are positioned within each of the two polypeptide chains from the N-terminus to the C-terminus of the polypeptide in the order: VH_BCMA-VL_CD16A-VH_CD16A-VL_BCMA (FIG. 1).

The variable domains are linked by linkers L1, L2 and L3 consisting of 12 or less amino acid residues and positioned within each of the two polypeptide chains from the N-terminus to the C-terminus in the order: VH_BCMA-L1-VL_CD16A-L2-VH_CD16A-L3-VL_BCMA.

Preferably, central linker L2 consists of 3 to 9, for example 3, 6 or 9 amino acid residues which is advantageous for bivalent binding to NK cells with high avidity, while NK-NK-cell cross linking is prevented. Further, linker L2 may be shorter than linkers L1 and L3, i.e. linker L2 consists of less amino acid residues than linkers L1 and L3. Longer more flexible linkers are advantageous for engaging (cross-linking) of NK cells through CD16A towards BCMA on myeloma cells.

In some embodiments the central linker L2 consists of 3 amino acid residues and the linkers L1 and L3 consist of 4, 5, 6, 7, 8, 9, 10, 11 or 12 amino acid residues, for example 6 to 9 or 6 to 12 amino acid residues. In particular embodiments the central linker L2 consists of 3 amino acid residues and the linkers L1 and L3 consist of 6, 9 or 12 amino acid residues. In other embodiments the central linker L2 consists of 6 amino acid residues and the linkers L1 and L3 consist of 7, 8, 9, 10, 11 or 12 amino acid residues, for example 9 to 12 amino acid residues.

In particular embodiments the central linker L2 consists of 3 amino acid residues and the linkers L1 and L3 consist of 9 or 12 amino acid residues or the central linker L2 consists of 6 amino acid residues and linkers L1 and L3 consists of 9 amino acid residues. Such linker combinations, e.g. 12/3/12, 9/3/9 and 9/6/9 are favorable for BCMA/CD16A tandem diabodies of the invention by enabling effective bivalent binding to CD16A as well as cross-linking to MM cells via BCMA. Short linkers L2 consisting of 3 or 6 amino acid residues are advantageous for the avidity of the bivalent CD16A antigen-binding portion of the tandem diabody according to the invention.

In a particular embodiment of the multispecific antigen-binding molecule comprising antigen-binding sites specifically binding to CD16A and BCMA the molecule comprises
  (i) a heavy chain variable domain specific for CD16A (VH_CD16A) and set forth in SEQ ID NO:8,
  (ii) a light chain variable domain specific for CD16A (VL_CD16A) and set forth in SEQ ID NO:9, In alternative embodiments, the heavy and light chain domains incorporate immunologically active homologues or variants of the CDR or framework sequences described herein. Accordingly in some embodiments, a CDR sequence in a heavy or light chain domain that binds to CD16A is similar to, but not identical to, the amino acid sequence depicted in SEQ ID NOs: 1-7. In certain instances, a CDR variant sequence has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of SEQ ID NOs: 1-7 and which is immunologically active.

In further instances, a CDR variant sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine.

In other instances, a CDR variant sequence is modified to change non-critical residues or residues in non-critical regions. Amino acids that are not critical can be identified by known methods, such as affinity maturation, CDR walking mutagenesis, site-directed mutagenesis, crystallization, nuclear magnetic resonance, photoaffinity labeling, or alanine-scanning mutagenesis.

In further alternative embodiments, the multispecific binding protein comprises heavy and light chain domains that are immunologically active homologues or variants of heavy and light chain domain sequences provided herein. Accordingly, in some embodiments, a multispecific binding protein comprises a heavy or light chain domain sequence that is similar to, but not identical to, the amino acid sequence depicted in SEQ ID NOs: 8-10. In certain instances, a variant heavy or light chain domain sequence has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of SEQ ID NOs: 8-10 and which is immunologically active.

In further instances, a variant heavy or light chain domain sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine.

In yet further instances, a variant heavy or light chain domain sequence incorporates substitutions that enhance properties of the CDR such as increase in stability, resistance to proteases and/or binding affinities to BCMA or CD16A.

In other instances, a variant heavy or light chain domain sequence is modified to change non-critical residues or residues in non-critical regions. Amino acids that are not critical can be identified by known methods, such as affinity maturation, CDR walking mutagenesis, site-directed mutagenesis, crystallization, nuclear magnetic resonance, photoaffinity labeling, or alanine-scanning mutagenesis.

The antigen-binding molecule according to any one of the embodiments described herein may be produced by expressing polynucleotides encoding the individual polypeptide chains which form the antigen-binding molecule. Therefore, further embodiments of the invention are polynucleotides, e.g. DNA or RNA, encoding the polypeptides of the antibody molecule as described herein above.

The polynucleotides may be constructed by methods known to the skilled person, e.g. by combining the genes encoding the variable domains either separated by peptide linkers or directly linked by a peptide bond of the polypeptide chains, into a genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotides in the respective host cell.

The polynucleotides may be inserted into vectors, preferably expression vectors, which represent a further embodiment of the invention. These recombinant vectors can be constructed according to methods well known to the person skilled in the art.

A variety of expression vector/host systems may be utilized to contain and express the polynucleotides encoding the polypeptide chains of the present invention. Examples for expression vectors for expression in *E. coli* are pSKK (LeGall et al., J Immunol Methods. (2004) 285(1):111-27) or pcDNA5 (Invitrogen) for the expression in mammal cells.

The invention further provides the multispecific antigen-binding molecule, in particular, a composition comprising a multispecific antigen-binding molecule as described herein above and at least one further component.

The invention further provides the multispecific antigen-binding molecule or a composition comprising the multispecific antigen-binding molecule as described herein above for use in a NK-cell based immunotherapy. NK-cell based immunotherapy includes active NK-cell based therapies in which NK-cells are activated through engagement by the antigen-binding molecule of the invention. In particular the ability of NK-cells for attacking and killing abnormal cells, such as cancer cells is enhanced.

In certain embodiments the invention provides a multispecific antigen-binding molecule specifically binding to CD16A and an antigen expressed on a myeloma cell or plasma cell selected from the group consisting of BCMA, CS-1, CD19, CD20, CD38 and CD138 as described above for the use in the treatment of multiple myeloma, comprising the step of administering the multispecific antigen-binding molecule.

In a certain embodiment the invention provides a multispecific antigen-binding molecule specifically binding to a target cell antigen, e.g. a tumor antigen, and CD16A for the use in NK-cell immunotherapy, wherein the multispecific antigen-binding molecule is mixed with NK-cells ex vivo and the composition of NK-cells and the multispecific antigen-binding molecule is administered to a patient.

In a particular embodiment the tumor antigen is BCMA and the composition is used for the treatment of a plasma cell disorder or autoimmune disease, in particular multiple myeloma.

Plasma cell disorders include multiple myeloma, plasmacytoma, plasma cell leukemia, macroglubulinemia, amyloidosis, Waldenstrom's macroglobulinemia, solitary bone plasmacytoma, extramedullary plasmacytoma, osteosclerotic myeloma, heavy chain disease, monoclonal gammopathy of undetermined significance (MGUS) and smoldering myeloma.

Autoimmune disease is for example systemic lupus erythematosus (SLE) or rheumatoid arthritis (RA).

Therefore, provided herein are in certain embodiments medical uses and methods wherein the antigen-binding protein specific for BCMA and CD16A, e.g. tandem diabody, as described herein above is administered in an effective dose to a subject for the treatment of a BCMA$^+$ cancer or autoimmune disease, for example multiple myeloma.

Administration is effected by different ways, e.g. by intravenous, intraperitoneal, subcutaneous, intramuscular, topical or intradermal administration. The dosage will be determined by the attending physician and other clinical factors. Dosages for any one subject depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology. An "effective dose" useful for treating and/or preventing a BCMA+ disease can be determined using known methods.

The following examples should further illustrate the described embodiments without limiting the scope of the invention. It is demonstrated that the particular bivalent CD16A engaging portion of a tandem diabody according to the invention is capable of inducing an enhanced NK cytotoxicity:

Example 1

Construction of BCMA/CD16A Tandem Diabody Molecules

The tandem diabodies are constructed as described in Reusch et al., 2014, mAbs 6:3, 728-739.

For constructing the tandem diabody the Fv domains of an anti-BCMA antibody clone are combined with the Fv domains of an anti-CD16A antibody clone. Antibody fragments with selective binding to a chosen target antigen can be isolated from a human antibody library by expression and display of single chain Fv domains (scFv) on filamentous fusion phage and enrichment of phage particles encoding scFv exhibiting target binding by panning on recombinant target antigen or target antigen-positive cells, as described, for example, in Smith GP (Science, 1985, 228: 1315-7) and Clackson et al. (Nature, 1991, 352: 624-8). To isolate BCMA-binding antibody fragments, recombinant human BCMA (1-54)-Fc, cynomolgus BCMA(1-53)-Fc and CHO cells stably expressing human BCMA(1-54) or cynomolgus BCMA(1-53) fused to the transmembrane region and cytoplasmic domain of human CD3zeta can be used in subsequent panning rounds to enrich binding phage particles. For this, phage particles are incubated with recombinant Fc-fusion antigen in solution, e.g. for 2 h at room temperature, followed by capture with Protein G-coated beads and washing in PBS-Tween and PBS to remove unbound phage. Bound phage is eluted with glycine. For enrichment of binding phage on target antigen-expressing cells, phage is incubated with stably transfected CHO cells, e.g. for 1 h at room temperature, followed by washing with cell culture medium and elution of bound phage with glycine. To reduce enrichment of phage particles encoding antibody fragments with selective binding to Fc or non-transfected CHO cells, phage pools are incubated with irrelevant Fc-fusion antigen or target antigen-negative CHO cells. Subsequent to each round of panning and elution of bound phage, eluted phage particles are used to infect *E. coli* (XL1 Blue) and propagate phage and scFv-encoding DNA. Following repeated phage panning and propagation of enriched phage clones, genetic DNA is isolated from *E. coli* and recloned into bacterial expression vectors, e.g. pSKK2, using standard molecular biology techniques for subsequent production of His-tagged (SEQ ID NO:12) scFv antibody fragments in *E. coli* and preparation of bacterial periplasmic extracts. Periplasmic extracts containing scFv antibody fragments are subjected to screening methods, such as ELISA or flow cytometry, to assess target antigen binding. For example, recombinant human BCMA(1-54)-Fc or cynomolgus BCMA(1-53)-Fc is bound by anti-human Fc antibody coated in standard ELISA microwell plates followed by incubation with bacterial periplasmic extracts and extensive washing. scFv binding is detected using anti-His-HRP conjugate. To assess scFv binding to cell-expressed BCMA, bacterial periplasmic extracts are incubated with CHO cells expressing human or cynomolgus BCMA followed by washing and detection of bound scFv using anti-His-R-PE by flow cytometry. Plasmids encoding scFv antibody fragments with selective binding to human and/or cynomolgus BCMA antigen are isolated from the respective bacterial clones and analyzed by DNA sequencing to obtain scFv encoding DNA sequences. For example anti-BCMA having an amino acid sequence as depicted in SEQ ID NO:19, wherein VH is depicted in SEQ ID NO:17 and VL is depicted in SEQ ID NO:18 has been obtained.

The expression cassette for the tandem diabody is cloned such that the anti-BCMA domains and the anti-CD16A domains are positioned in the order VH_BCMA-L1-VL_CD16A-L2-VH_CD16A-L3-VL_BCMA and $(G_2S)_4$ is used for linkers L1 and L3 and $(G_2S)$ is used for linker L2 in the tandem diabody according to the invention.

The expression cassette for the tandem diabody is cloned into a mammalian expression vector and the tandem diabody is produced and purified as described.

Example 2

Antibody Binding to Primary NK-Cells

Method: Serial dilutions of tandem diabodies with specificity for BCMA and CD16A in variant 2 and variant 4 are added to primary human NK-cells at 37° C. for 45 min in presence or absence of 10 mg/mL polyclonal human IgG (Gammanorm, Octapharma) followed by detection of antibody binding on ice by repeated washing with buffer, incubation with recombinant human BCMA(1-54)-GCN4-His fusion protein for 30 min, repeated washing and addition of mouse anti-His mAb 13/45/31-2 (Dianova) and FITC-conjugated goat anti-mouse IgG before flow cytometric analysis.

Results are shown in Table 1 and FIG. 3: The tested tandem diabodies in variant 2 and variant 4 interact with comparable apparent affinity ($K_D$: 2.1 nM and 1.2 nM, respectively) with primary human NK-cells. Notably, while binding affinity of both molecules is reduced upon addition of 10 mg/mL polyclonal IgG, variant 2 and variant 4 antibodies are differentially affected. Addition of IgG reduces the apparent affinity of variant 2 and variant 4 tandem diabody 6.9-fold ($K_D$: 14.5 nM) and 3-fold ($K_D$: 3.6 nM), respectively, suggesting that the domain order used in variant 4, i.e. positioning of CD16A-directed Fv domains in both central positions of the tandem diabody, impacts NK-cell binding and results in reduced competition by polyclonal IgG for CD16A.

TABLE 1

Tandem diabody binding to primary NK-cells

| Antibody | $K_D$ (Buffer) | $K_D$ (10 mg/mL IgG) | fold-change |
|---|---|---|---|
| Variant 2 | 2.1 nM | 14.5 nM | 6.9 |
| Variant 4 | 1.2 nM | 3.6 nM | 3.0 |

Method: Serial dilutions of anti-CD16A scFv are added to primary human NK-cells at 37° C. for 45 min followed by detection of antibody binding on ice. Tandem diabody detection is performed by repeated washing with buffer, incubation with recombinant BCMA(1-54)-GCN4-His and addition of mouse anti-His mAb 13/45/31-2 (Dianova) and FITC-conjugated goat anti-mouse IgG followed by flow cytometric analysis. Anti-CD16A scFv is detected as tandem diabody by repeated washing with buffer, incubation with anti-His mAb 13/45/31-2 (Dianova) and FITC-conjugated goat anti-mouse IgG followed by flow cytometric analysis.

Results are shown in Table 2 and FIG. 4: Tandem diabody in variant 4 interacts with primary human NK-cells with an apparent affinity ($K_D$) of 1.2 nM, while the corresponding anti-CD16A scFv exhibits an affinity of 12.2 nM ($K_D$). The observed increase in avidity suggests bivalent CD16A binding of tandem diabody on NK-cells.

TABLE 2

Tandem diabody and anti-CD16A scFv binding to primary human NK-cells

| Antibody | $K_D$ (Buffer) |
|---|---|
| Variant 4 | 1.2 nM |
| Anti-CD16A scFv | 12.2 nM |

NK-Cell Surface Retention of Tandem Diabody in Presence and Absence of Polyclonal Human IgG Methods: Primary human NK-cells are incubated with 50 μg/mL BCMA/CD16A-directed tandem diabody in variant 4 for 45 min on ice, followed by centrifugation and resuspension in buffer containing 10 mg/mL polyclonal human IgG (Gammanorm, Octapharma) or no IgG and incubation at 37° C. Antibody dissociation is monitored by quantifying the relative amount of tandem diabody bound on NK-cells after 5, 10, 15, 20, 25, 30, 45 and 60 min by sequential staining with BCMA(1-54)-GCN4-His, mAb anti-His and FITC-conjugated goat anti-mouse IgG and subsequent flow cytometric analysis.

Results are shown in FIG. 5: Tandem diabody retention on the NK-cell surface is not affected by addition of polyclonal IgG, as the rate of dissociation is similar in presence and absence of IgG (approx. 70% bound antibody after 1 h dissociation time). These data suggest that polyclonal IgG cannot compete with tandem diabody binding to NK-cells and indicate binding of tandem diabody to an epitope distinct from the binding site of IgG on CD16A. Consequently, BCMA/CD16A-directed tandem diabody in variant 4 may be uniquely suited to bind NK-cells in presence of serum IgG, e.g. at physiological IgG concentrations and in particular in plasma cell disorders, characterized by high level production of monoclonal immunoglobulin. In particular, the observed retention of tandem diabody on NK-cells and the lack of IgG interference with its dissociation suggest tandem diabody in variant 4 may be used in combination with cellular NK-cell products, e.g. by mixing NK-cells and antibody ex vivo before infusion into patients (adoptive NK-cell transfer). Because classical IgG-based therapeutic antibody formats interact only weakly with CD16A and directly compete with serum IgG for CD16A binding, it is expected that CD16A-directed tandem diabody in variant 4 enables novel combination approaches with cellular NK-cell products that have, so far, been impossible to realize.

Example 3

Antibody-Induced NK-Cell-Mediated Cytotoxicity

Methods: Antibody-induced NK-cell-mediated cytotoxicity towards BCMA+ myeloma cell line NCI-H929 is tested in vitro by incubating human primary NK-cells and calcein-labeled NCI-H929 target cells at a ratio of 5:1 in presence of increasing concentration of BCMA/CD16A-directed tandem diabody in variant 2 and variant 4. Assays are performed in presence and absence of 10 mg/mL polyclonal human IgG (Gammanorm, Octapharma). Specific target cell lysis is assessed by quantifying calcein-release into cell culture supernatant after 4 hours incubation at 37° C.

Results are shown in Table 3 and FIG. 6: Antibody-induced target cell lysis is observed with all antibodies tested. Tandem diabody in variant 2 induces half maximal target cell lysis ($EC_{50}$) at 78.3 pM and 3782.0 pM in absence and presence of 10 mg/mL polyclonal human IgG, respectively, corresponding to a loss of potency of 48.3-fold. Notably, addition of IgG reduces antibody efficacy (% target cell lysis) from approximately 90% to 70%. In contrast, $EC_{50}$ of tandem diabody in variant 4 is markedly less affected by addition of IgG. While tandem diabody in variant 4 induces half maximal target cell lysis at 16.2 pM in absence of IgG, and is therefore significantly more potent than tandem diabody variant 2, addition of IgG increases $EC_{50}$ only to 76.1 pM (=4.7-fold loss in potency). Furthermore, efficacy of target cell lysis is reduced from approx. 100% to 90%. Consequently, reformatting of BCMA/CD16A-directed tandem diabody from variant 2 to variant 4 significantly improves in vitro potency and efficacy of NK-cell-mediated target cell lysis. These data suggest BCMA/CD16A-directed tandem diabody in variant 4 may be particularly suited to engage NK-cells for therapeutic use in presence of serum IgG, e.g. at physiological concentrations of IgG and in the context of plasma cell orders characterized by high level production of IgG, such as multiple myeloma.

TABLE 3

Antibody-induced NK-cell-mediated cytotoxicity towards BCMA+ myeloma cell lines in vitro

| Antibody | $EC_{50}$ (Buffer) | $EC_{50}$ (10 mg/mL) | Fold-loss in potency |
|---|---|---|---|
| Variant 2 | 78.3 pM | 3782.0 pM | 48.3 |
| Variant 4 | 16.2 pM | 76.1 pM | 4.7 |

Example 4

Antibody-Induced NK-Cell-Mediated NK-Cell Lysis In Vitro

Methods: Calcein-labeled primary human NK-cells are incubated with increasing concentrations of BCMA/CD16A-directed tandem diabodies in variant 2 and variant 4. Antibody-induced NK-cell lysis is assessed by quantifying calcein-release into cell culture supernatant after 4 hours of incubation at 37° C.

Results are shown in Table 4 and FIG. 7: Tandem diabody in variant 2 induces approx. 60% of NK-cell lysis with half maximal lysis ($EC_{50}$) observed at 492.7 pM, and hence results in significant depletion of effector cells. In contrast, tandem diabody in variant 4 does not induce NK-cell lysis despite its higher apparent affinity compared with tandem diabody in variant 2 and its ability to bivalently engage CD16A on NK-cells. These data suggest the changed domain order in variant 4 results in a protein conformation in which both CD16A-directed Fv domains are positioned such that bivalent binding is optimal but NK-cell-NK-cell cross-linking is prevented. Consequently, variant 4 tandem diabodies may be used at higher therapeutic concentrations without inducing NK-cell depletion. Furthermore, the failure to induce NK-cell-NK-cell lysis may allow variant 4 tandem diabodies to be used in combination with cellular NK-cell therapies, e.g. by mixing allogeneic or autologous NK-cells and antibody ex vivo before infusion into patients (adoptive transfer).

TABLE 4

NK-cell-NK-cell lysis is induced by variant 2 but not variant 4 tandem diabody

| Antibody | $EC_{50}$ |
|---|---|
| Variant 2 | 4927 pM |
| Variant 4 | — |

NK-Cell-NK-Cell Lysis is Induced by Bivalent, Monospecific Anti-CD16A Diabody

Methods: Calcein-labeled primary human NK-cells are incubated with increasing concentrations of monospecific CD16A-directed monovalent scFv and bivalent diabody. Antibody-induced NK-cell lysis is assessed by quantifying calcein-release into cell culture supernatant after 4 hours of incubation at 37° C.

Results are shown in Table 5 and FIG. 8: Anti-CD16A diabody induces NK-cell lysis ($EC_{50}$: 659.2 pM), while monovalently binding anti-CD16A scFv does not induce detectable NK-cell depletion. Of note, anti-CD16A diabody is a homodimer of two polypeptides, each incorporating light and heavy chain variable domains in VL_CD16A-VH_CD16A domain order as used in the center of BCMA/CD16A-directed tandem diabody in variant 4. However, while anti-CD16A diabody potently induces NK-cell depletion in vitro, no NK-cell depletion is observed with variant 4 tandem diabody. These data suggest the VL_CD16A-VH_CD16A moiety of variant 4 tandem diabody adopts a structural conformation that is dissimilar from a classical diabody and prevents NK-cell-NK-cell cross-linking.

TABLE 5

NK-cell-NK-cell lysis is induced by bivalent, monospecific anti-CD16A diabody

| Antibody | $EC_{50}$ |
|---|---|
| Anti-CD16A scFv | — |
| Anti-CD16A diabody | 659.2 pM |

TABLE 6

Domain order of antibody constructs

| Antibody | Domain order |
|---|---|
| tandem diabody variant 2 | VH_CD16A-VL_BCMA-VH_BCMA-VL_CD16A |
| tandem diabody variant 4 | VH_BCMA-VL_CD16A-VH_CD16A-VL_BCMA |

TABLE 6-continued

Domain order of antibody constructs

| Antibody | Domain order |
|---|---|
| Anti-CD16A diabody | VL_CD16A-VH_CD16A |
| Anti-CD16A scFv | VL_CD16A-VH_CD16A |

Example 5

Antibody-Induced Cytokine Release in Human PBMC Cultures in Presence and Absence of BCMA+ Target Cells Methods: Production of inflammatory cytokines (IL-4, IL-2, IL-10, IL-6, TNFα and IFN-γ) in human PBMC cultures mixed with BCMA+ target cells (NCI-H929) in a ratio of 50:1 in presence or absence of increasing concentrations of anti-BCMA IgG1, anti-BCMA IgG1 bearing CD16A affinity-enhancing mutations S239D/I332E, BCMA/CD16A-directed tandem diabody in variant 4 and BCMA/CD3-directed (scFv)$_2$ is quantified following 24 h of incubation at 37° C. As control, cytokine release is stimulated by addition of CD3/CD28-targeting beads.

Results are shown in FIG. 9: Significant release of inflammatory cytokines IL-2, IL-10, IL-6, TNFα and IFN-γ is detected in PBMC/NCI-H929 co-cultures when T-cell-engaging BCMA/CD3-directed (scFv)$_2$ is added at concentrations of 3.2 ng/mL or above. Cytokine release following non-physiological T-cell activation using antibodies can result in significant toxicity in patients, including cytokine release syndrome. Induction of target cell lysis with BCMA/CD16A-directed tandem diabody to stimulate NK-cell-mediated cytotoxicity does result in markedly lower amounts of inflammatory cytokines released into cell culture supernatants that are comparable to cytokine release induced by classical BCMA-targeting IgG1 (WT) and affinity-enhanced IgG1 (Fc-enhanced; S239D/I332E). Consequently, CD16A-directed NK-cell-engagement to induce target cell lysis may be a safer alternative to T-cell-engagement due to a reduced risk of cytokine release syndrome and associated toxicity.

Example 6

Antibody-Induced NK-Cell-Mediated Cytotoxicity Towards BCMA+ Cell Lines

Methods: Antibody-induced NK-cell-mediated cytotoxicity towards BCMA$^+$ myeloma cell lines NCI-H929, RPMI-8226 and MM.1S is tested in vitro by incubating human primary NK-cells and calcein-labeled BCMA+ target cells at a ratio of 5:1 in presence of increasing concentration of BCMA/CD16A-directed tandem diabody or comparator IgG1 antibodies specific for CS1 (elotuzumab), CD38 (daratumumab) and EGFR (cetuximab). Specific target cell lysis is assessed by quantifying calcein-release into cell culture supernatant after 4 hours incubation at 37° C.

Results are shown in FIG. 10 and table 7: BCMA/CD16A-directed tandem diabody (tandem diabody variant 4) potently induces NK-cell-mediated lysis of MM.1S, NCI-H929 and RPMI-8226 cell lines with EC50 values of 3.7 pM, 9.1 pM, and 62.3 pM, respectively. Both potency and percentage of target cell lysis was comparable or superior to lysis induced by classical IgG1 antibodies elotuzumab and daratumumab. No lysis was observed when assays were performed in presence of increasing concentrations of anti-EGFR IgG1. Strikingly, BCMA/CD16A-directed tandem diabody induced comparable or superior target cell lysis despite markedly lower BCMA expression on the tested cell lines.

TABLE 7

In vitro cytotoxicity of primary human NK-cells towards BCMA+ target cell lines in presence of increasing concentrations of BCMA/CD16A-directed tandem diabody and comparator antibodies.

| Antibody | EC$_{50}$ | | |
|---|---|---|---|
| | MM1.S | NCI-H929 | RPM-8226 |
| Tandem diabody (variant 4) | 3.7 pM | 9.1 pM | 62.3 pM |
| Anti-CD38 IgG1 | 51.0 pM | 12.6 pM | 41.8 pm |
| Anti-CS1 IgG1 | 152.8 pM | 393.7 pM | 4.5 nM |
| Cetuximab | — | — | — |

Example 7

Antibody-Induced NK-Cell-Mediated Cytotoxicity Towards Primary Myeloma Cells

Methods: Antibody-induced NK-cell-mediated cytotoxicity towards primary myeloma cells taken from heavily pretreated patients is tested in vitro by incubating human primary NK-cells and $^{51}$Cr-labeled tumor cells at a ratio of 10:1 in presence of increasing concentration of BCMA/CD16A-directed tandem diabody or comparator IgG1 antibodies specific for CS1 (elotuzumab), CD38 (daratumumab) and Her2 (trastuzumab). Specific target cell lysis is assessed by quantifying $^{51}$Cr-release into cell culture supernatant after 4 hours incubation at 37° C.

Results are shown in FIG. 11 and table 8: BCMA/CD16A-directed tandem diabody (tandem diabody variant 4) potently induces NK-cell-mediated lysis of primary myeloma cells taken from a pleural effusion (left panel) or peripheral blood (plasma cell leukemia, right panel). In comparison, less potent induction of target lysis is observed when anti-CD38 and anti-CS1 antibodies daratumumab and elotuzumab are used, respectively. No target cell lysis is detected when assays were performed in presence of increasing concentrations of anti-Her2 IgG1 antibody trastuzumab. EC50 values are shown in table 8.

TABLE 8

In vitro cytotoxicity of primary human NK-cells towards primary myeloma cells in presence of increasing concentrations of BCMA/CD16A-directed tandem diabody and comparator antibodies.

| Antibody | EC$_{50}$ | |
|---|---|---|
| | Multiple myeloma | Plasma cell leukemia |
| Tandem diabody (v4) | 4.0 pM | 6.3 pM |
| Daratumumab | 17.7 pM | 15.7 pM |
| Elotuzumab | 145.5 pM | 78.2 pM |
| Trastuzumab | — | — |

Example 8

Antibody Binding to Myeloma Cell Lines

Methods: BCMA/CD16A-directed tandem diabody and comparator antibodies specific for CD38 (daratumumab) and CS1 (elotuzumab) were titrated on cell lines NCI-H929, RPMI-8226 and MM.1S. Antibody binding was quantified by detection with CD16A-mFc.67/anti-human-FITC and flow cytometry, control antibodies anti-BCMA (ANC3B1), anti-CD38 (HB7) and anti-CS1 (235614) were added at saturating concentrations and detected by anti-mouse-Fc-FITC (ctrl.)

Results are shown in FIG. 12 and table 9: BCMA/CD16A-directed tandem diabody (tandem diabody variant 4) binds MM.1S, NCI-H929 and RPMI-8226 myeloma cell lines with K$_D$ values of 11.5 nM, 27.7 nM and 26.7 nM, respectively. In comparison, anti-CD38 IgG1 antibody daratumumab interacts with all three cell lines with markedly higher affinity (0.74 nM, 2.2 nM and 6.2 nM, respectively. Anti-CS1 IgG1 antibody elotuzumab interacts with MM.1S and NCI-H929 cells with lower affinity when compared with BCMA/CD16A-directed tandem diabody and anti-CD38 IgG1 daratumumab (35.7 nM and 36 nM, respectively) and does not interact with RPMI-8226 due to lack of CS1 expression. Of note, comparison of mean fluorescence intensities (MFI) suggests significantly lower BCMA expression on all three cell lines when compared with CD38 expression. However, despite low BCMA expression and lower binding target cell binding affinity compared with anti-CD37 IgG1 daratumumab, BCMA/CD16A-directed tandem diabody induced NK-cell-mediated target cell lysis with similar or better potency than anti-CD38 IgG1 daratumumab.

TABLE 9

Antibody binding to myeloma cell lines.

| Antibody | K$_D$ | | |
|---|---|---|---|
| | MM1.S | NCI-H929 | RPMI-8226 |
| Tandem diabody (v4) | 11.5 nM | 27.7 nM | 26.7 nM |
| Anti-CD38 IgG1 | 0.74 nM | 2.2 nM | 6.2 nM |
| Anti-CS1 IgG1 | 35.7 nM | 36.0 nM | — |
| Cetuximab | — | — | — |

Example 9

Antibody-Induced NK-Cell-Mediated NK-Cell Lysis In Vitro Independent from Target Domain Methods: Calcein-labeled primary human NK-cells were incubated with increasing concentrations of the indicated tandem diabodies in variant 2 and variant 4. Antibody-induced NK-cell lysis was assessed by quantifying calcein-release into cell culture supernatant after 4 hours of incubation at 37° C.

Results: Tandem diabodies in variant 2 induced substantial NK-NK lysis whereas variant 4 tandem diabodies didn't. This difference between variant 2 and variant 4 was observed for tandem diabodies containing an anti-BCMA target domain as well as for tandem diabodies containing a target domain towards a peptide/MHC complex with the HLA-A2 restricted peptide metalloproteinase 1 (MMP1). The data shows that the enhanced NK cell cytotoxicity against the target cells is driven by the specific protein conformation of the specific CD16A Fv-domains incorporated in the tandem diabody and does not depend on a particular target domain. Apparently, the enhanced activation of NK cells does neither depend on the tumor target domain nor on the kind of tumor target.

TABLE 10

Tabulated summary of 4 h calcein-release cytotoxicity assays to assess antibody-induced NK-NK cell lysis

| target domain | effector domain | variant | EC$_{50}$ [pM] |
|---|---|---|---|
| BCMA | CD16A | 2 | 493 |
| BCMA | CD16A | 4 | no |

TABLE 10-continued

Tabulated summary of 4 h calcein-release cytotoxicity assays to assess antibody-induced NK-NK cell lysis

| target domain | effector domain | variant | EC$_{50}$ [pM] |
|---|---|---|---|
| HLA-A2 | CD16A | 2 | 1296 |
| HLA-A2 | CD16A | 4 | no |

Var = tandem diabody variant; no = no NK cell lysis

The HLA-A2 binding peptide originates from matrix metallopeptidase 1 (MMP1) and was identified as a promising therapeutic target presented by several tumor types, including colorectal and lung cancer, but absent on normal tissues (MMP1-003 disclosed in WO 2016/156202). HLA-A2 specific single chain Fv antibodies were identified by screening a fully human antibody phage display library with MMP-003. HLA-A2/CD16A tandem diabody in variant 2 and HLA-A2/CD16A tandem diabody in variant 4 according to the invention were created.

```
                        Sequence Summary:

SEQ
NO.  Sequence

1  HCDR1 CD16A
     GYTFTSYY

2  HCDR2 CD16A
     IEPMYGST

3  HCDR3 CD16A
     ARGSAYYYDFADY

4  LCDR1 CD16A
     NIGSKN

5  LCDR2 CD16A
     QDN

6  LCDR3 CD16A
     QVWDNYSVL

7  HCDR2 CD16A
     INPSGGST

8  VH CD16A
     QVQLVQSGAEVKKPGESLKVSCKASGYTFTSYYMHWVRQAPGQGLEWMGAIEPMYGSTSYAQK
     FQGRVTMTRDTSTSTVYMELSSLRSEDTAVYYCARGSAYYYDFADYWGQGTLVTVSS

9  VL CD16A
     SYVLTQPSSVSVAPGQTATISCGGHNIGSKNVHWYQQRPGQSPVLVIYQDNKRPSGIPERFSG
     SNSGNTATLTISGTQAMDEADYYCQVWDNYSVLFGGGTKLTVL

10  VH CD16A
     QVQLVQSGAEVKKPGESLKVSCKASGYTFTSYYMHWVRQAPGQGLEWMGIINPSGGSTSYAQK
     FQGRVTMTRDTSTSTVYMELSSLRSEDTAVYYCARGSAYYYDFADYWGQGTLVTVSS

11  C-terminal sequence of CD16A
     SFFPPGYQ

12  Affinity-Tag
     AAAGSHHHHHH

13  Linker
     GGSG

14  Linker
     GGSGG

15  Linker
     GGSGGS

16  Linker
     GGSGGSGGS

17  BCMA VH
     QVQLVQSGAEVKTPGEPLKISCKGSGYSFTDSWIGWVRQMPGKGLEWMGIIYAGDSDARYSPS
     FQGQVTISADTSTSTVYLQWSSLKASDTAMYYCARNFGDHWGQGTLVTVSS
```

Sequence Summary:

| SEQ NO. | Sequence |
|---|---|
| 18 | BCMA VL<br>SYELTQSPSVSVAPGQTARIFCGGDNIGSKNVHWYQQKPGQAPVLVIYRDSNRPSGIPERFSG<br>ANSENTATLTISRAQAGDEADYYCQVWDSRTYVFGTGTKLTVL |
| 19 | BCMA scFv<br>QVQLVQSGAEVKTPGEPLKISCKGSGYSFTDSWIGWVRQMPGKGLEWMGIIYAGDSDARYSPS<br>FQGQVTISADTSTSTVYLQWSSLKASDTAMYYCARNFGDHWGQGTLVTVSSGGSGGSGGSGGS<br>GGSGGSSYELTQSPSVSVAPGQTARIFCGGDNIGSKNVHWYQQKPGQAPVLVIYRDSNRPSGI<br>PERFSGANSENTATLTISRAQAGDEADYYCQVWDSRTYVFGTGTKLTVLAAAGSHHHHHH |
| 20 | CD16A<br>GMRTEDLPKAVVFLEPQWYRVLEKDSVTLKCQGAYSPEDNSTQWFHNESLISSQASSYFIDAA<br>TVDDSGEYRCQTNLSTLSDPVQLEVHIGWLLLQAPRWVFKEEDPIHLRCHSWKNTALHKVTYL<br>QNGKGRKYFHHNSDFYIPKATLKDSGSYFCRGLFGSKNVSSETVNITITQGLAVSTISSFFPP<br>GYQ |
| 21 | Linker $(G_2S)_4$<br>GGSGGSGGSGGS |

The invention claimed is:

1. A dimeric multispecific antigen-binding molecule specifically binding to CD16A and a target cell antigen different from CD16A consisting of two polypeptide chains, wherein each polypeptide chain comprises at least four variable domains selected from the group consisting of:
   (i) a heavy chain variable domain specific for CD16A (VH_CD16A) comprising a heavy chain CDR1 comprising the amino acid sequence set forth in SEQ ID NO:1; a heavy chain CDR2 comprising the amino acid sequence set forth in SEQ ID NO:7; a heavy chain CDR3 comprising the amino acid sequence set forth in SEQ ID NO:3,
   (ii) a light chain variable domain specific for CD16A (VL_CD16A) comprising a light chain CDR1 comprising an amino acid sequence set forth in SEQ ID NO:4; a light chain CDR2 comprising an amino acid sequence set forth in SEQ ID NO:5; and a light chain CDR3 comprising an amino acid sequence set forth in SEQ ID NO:6,
   (iii) a heavy chain variable domain specific for the target cell antigen (VH_TA), and
   (iv) a light chain variable domain specific for the target cell antigen (VL_TA),
   wherein
   these variable domains are linked one after another by peptide linkers L1, L2 and L3 consisting of 12 or less amino acid residues and positioned within each of the two polypeptide chains from the N-terminus to the C-terminus in the order:
   VH TA-L1-VL_CD16A-L2-VH_CD16A-L3-VL TA.

2. The multispecific antigen-binding molecule of claim 1, wherein linker L2 consists of less amino acid residues than each of linkers L1 and L3.

3. The multispecific antigen-binding molecule of claim 1, wherein linker L2 consists of 3 to 9 amino acid residues.

4. The antigen-binding molecule of claim 3, wherein (i) linker L2 consists of 3 amino acid residues and each of linkers L1 and L3 consists of 6 to 12 amino acid residues or (ii) linker L2 consists of 6 amino acid residues and each of linkers L1 and L3 consists of 9 to 12 amino acid residues.

5. The multispecific antigen-binding molecule of claim 4, wherein (i) linker L1 consists of 12 amino acid residues, linker L2 consists of 3 amino acid residues and linker L3 consists of 12 amino acid residues or (ii) linker L1 consists of 9 amino acid residues, linker L2 consists of 6 amino acid residues and linker L3 consists of 9 amino acid residues.

6. The multispecific antigen-binding molecule of claim 1, wherein the target cell antigen is selected from the group consisting of BCMA, CS-1, CD19, CD20, CD38, and CD138.

7. The multispecific antigen-binding molecule of claim 1, wherein (i) the heavy chain variable domain specific for CD16A comprising the amino acid sequence set forth in SEQ ID NO:10 (VH_CD16A), and (ii) the light chain variable domain specific for CD16A comprising the amino acid sequence set forth in SEQ ID NO:9 (VL_CD116A).

8. A polynucleotide encoding a multispecific antigen-binding molecule of claim 1.

9. A vector comprising a polynucleotide of claim 8.

10. A host cell transfected with a vector of claim 9.

11. A method for treating multiple myeloma, comprising administering to a subject in need thereof the multispecific antigen-binding molecule of claim 6, wherein the target cell antigen is BCMA.

* * * * *